United States Patent
Horseman et al.

(10) Patent No.: US 10,628,770 B2
(45) Date of Patent: Apr. 21, 2020

(54) SYSTEMS AND METHODS FOR ACQUIRING AND EMPLOYING RESILIENCY DATA FOR LEADERSHIP DEVELOPMENT

(71) Applicant: Saudi Arabian Oil Company, Dhahran (SA)

(72) Inventors: Samantha J. Horseman, Dhahran (SA); Brent Mattson, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1095 days.

(21) Appl. No.: 14/968,095

(22) Filed: Dec. 14, 2015

(65) Prior Publication Data

US 2017/0169379 A1 Jun. 15, 2017

(51) Int. Cl.
*G06Q 10/06* (2012.01)
*G16H 10/20* (2018.01)
(Continued)

(52) U.S. Cl.
CPC ... *G06Q 10/06393* (2013.01); *G02B 27/0172* (2013.01); *G06Q 10/00* (2013.01);
(Continued)

(58) Field of Classification Search
CPC ... G06Q 10/06393; G06Q 10/00; G16H 50/30
See application file for complete search history.

(56) References Cited

U.S. PATENT DOCUMENTS

| 4,951,963 A | 8/1990 | Behr et al. |
| 4,998,534 A | 3/1991 | Claxton, III et al. |

(Continued)

FOREIGN PATENT DOCUMENTS

| AU | 767533 B2 | 11/2003 |
| CN | 101065752 A | 10/2007 |

(Continued)

OTHER PUBLICATIONS

"Augmented Reality", retrieved from <http://en.wikipedia.org/wiki/Augmented_reality>, May 30, 2012. pp. 1-18.
(Continued)

*Primary Examiner* — Nadja N Chong Cruz
(74) *Attorney, Agent, or Firm* — Bracewell LLP; Constance G. Rhebergen; Christopher L. Drymalla

(57) ABSTRACT

Provided in some embodiments are systems and methods for acquiring and employing resiliency data for leadership development. Provided in some embodiments is a method that includes acquiring a set of resiliency data for an employee, determining a resiliency score for the employee based at least in part on the set of resiliency data, determining that the employee is recommended for promotion to a leadership position within an organization based at least in part on the resiliency score, determining a ranking of the employee relative to other employees within the organization based at least in part on the resiliency score, and serving, to a first device for display to the employee, an employee leadership review dashboard including an indication of the resiliency score for the employee, and an indication of the ranking of the employee relative to the other employees.

21 Claims, 15 Drawing Sheets

(51) Int. Cl.
*G16H 40/63* (2018.01)
*G16H 50/30* (2018.01)
*G06Q 10/00* (2012.01)
*G09B 5/02* (2006.01)
*G02B 27/01* (2006.01)
*G06T 19/00* (2011.01)

(52) U.S. Cl.
CPC .............. *G06T 19/006* (2013.01); *G09B 5/02* (2013.01); *G16H 10/20* (2018.01); *G16H 40/63* (2018.01); *G16H 50/30* (2018.01); *G02B 2027/0141* (2013.01)

(56) References Cited

U.S. PATENT DOCUMENTS

| | | | |
|---|---|---|---|
| 5,000,188 | A | 3/1991 | Kojima |
| 5,111,539 | A | 5/1992 | Hiruta et al. |
| 5,253,656 | A | 10/1993 | Rincoe et al. |
| 5,304,112 | A | 4/1994 | Mrklas et al. |
| 5,305,238 | A | 4/1994 | Starr, III |
| 5,323,650 | A | 6/1994 | Fullen et al. |
| 5,331,549 | A | 7/1994 | Crawford, Jr. |
| 5,343,869 | A | 9/1994 | Pross et al. |
| 5,410,471 | A | 4/1995 | Alyfuku et al. |
| 5,435,315 | A | 7/1995 | McPhee et al. |
| 5,441,047 | A | 8/1995 | David |
| 5,542,420 | A | 8/1996 | Goldman et al. |
| 5,570,301 | A | 10/1996 | Barrus |
| 5,573,269 | A | 11/1996 | Gentry et al. |
| 5,626,145 | A | 5/1997 | Clapp et al. |
| 5,673,691 | A | 10/1997 | Abrams et al. |
| 5,722,418 | A | 3/1998 | Bro |
| 5,792,047 | A | 8/1998 | Coggins |
| 5,813,993 | A | 9/1998 | Kaplan et al. |
| 5,926,806 | A | 7/1999 | Marshall et al. |
| 5,937,387 | A | 8/1999 | Summerell et al. |
| 6,033,344 | A | 3/2000 | Trulaske et al. |
| 6,049,281 | A | 4/2000 | Osterweil |
| 6,080,106 | A | 6/2000 | Lloyd et al. |
| 6,083,156 | A | 7/2000 | Lisiecki |
| 6,104,296 | A | 8/2000 | Yasuchi et al. |
| 6,148,280 | A | 11/2000 | Kramer |
| 6,149,586 | A | 11/2000 | Elkind |
| 6,190,314 | B1 | 2/2001 | Ark et al. |
| 6,198,394 | B1 | 3/2001 | Jacobsen et al. |
| 6,203,495 | B1 | 3/2001 | Bardy |
| 6,269,339 | B1 | 7/2001 | Silver |
| 6,281,594 | B1 | 8/2001 | Sarich |
| 6,291,900 | B1 | 9/2001 | Tiemann et al. |
| 6,293,771 | B1 | 9/2001 | Haney et al. |
| 6,307,476 | B1 | 10/2001 | Smith et al. |
| 6,309,342 | B1 | 10/2001 | Blazey et al. |
| 6,334,837 | B1 | 1/2002 | Hein et al. |
| 6,345,839 | B1 | 2/2002 | Kuboki et al. |
| 6,353,764 | B1 | 3/2002 | Imagawa et al. |
| 6,369,337 | B1 | 4/2002 | Machiyama et al. |
| 6,381,577 | B1 | 4/2002 | Brown |
| 6,383,136 | B1 | 5/2002 | Jordan |
| 6,408,263 | B1 | 6/2002 | Summers |
| 6,425,862 | B1 | 7/2002 | Brown |
| 6,450,530 | B1 | 9/2002 | Frasher et al. |
| 6,452,862 | B1 | 9/2002 | Tomotani |
| 6,546,286 | B2 | 4/2003 | Olson |
| 6,572,558 | B2 | 6/2003 | Masakov et al. |
| 6,585,645 | B2 | 7/2003 | Hutchinson |
| 6,594,607 | B2 | 7/2003 | Lavery |
| 6,646,556 | B1 | 11/2003 | Smith et al. |
| 6,648,820 | B1 | 11/2003 | Sarel |
| 6,658,572 | B1 | 12/2003 | Craig |
| 6,669,286 | B2 | 12/2003 | Iusim |
| 6,673,027 | B2 | 1/2004 | Fischer |
| 6,675,130 | B2 | 1/2004 | Kanevsky et al. |
| 6,692,258 | B1 | 2/2004 | Kurzweil |
| 6,705,990 | B1 | 3/2004 | Gallant et al. |
| 6,736,642 | B2 | 5/2004 | Bajer |
| 6,767,330 | B2 | 7/2004 | Lavery et al. |
| 6,768,246 | B2 | 7/2004 | Pelrine et al. |
| 6,781,067 | B2 | 8/2004 | Montagnino et al. |
| 6,828,908 | B2 | 12/2004 | Clark |
| 6,832,987 | B2 | 12/2004 | David et al. |
| 6,850,798 | B2 | 2/2005 | Morgan |
| 6,918,769 | B2 | 7/2005 | Rink |
| 6,931,359 | B2 | 8/2005 | Tamada |
| 6,982,497 | B2 | 1/2006 | Rome |
| 7,005,757 | B2 | 2/2006 | Pandian |
| 7,027,621 | B1 | 4/2006 | Prokoski |
| 7,063,665 | B2 | 6/2006 | Hasegawa et al. |
| 7,074,198 | B2 | 7/2006 | Krullaards |
| 7,104,965 | B1 | 9/2006 | Jiang et al. |
| 7,109,872 | B2 | 9/2006 | Balaban et al. |
| 7,128,577 | B2 | 10/2006 | Renaud |
| 7,152,024 | B2 | 12/2006 | Marschner |
| 7,155,158 | B1 | 12/2006 | Iuppa |
| 7,163,489 | B1 | 1/2007 | Nelson |
| 7,188,151 | B2 | 3/2007 | Kumar et al. |
| 7,233,312 | B2 | 6/2007 | Stern et al. |
| 7,273,453 | B2 | 9/2007 | Shallenberger |
| 7,304,580 | B2 | 12/2007 | Sullivan et al. |
| 7,315,249 | B2 | 1/2008 | Littell |
| 7,351,206 | B2 | 4/2008 | Suzuki |
| 7,399,276 | B1 | 7/2008 | Brown et al. |
| 7,407,484 | B2 | 8/2008 | Korman |
| 7,481,779 | B2 | 1/2009 | Large |
| 7,598,881 | B2 | 10/2009 | Morgan |
| 7,624,037 | B2 | 11/2009 | Bost |
| 7,652,582 | B2 | 1/2010 | Littell |
| 7,689,271 | B1 | 3/2010 | Sullivan |
| 7,717,866 | B2 | 5/2010 | Damen |
| 7,771,318 | B2 | 8/2010 | Narayanaswami |
| 7,830,249 | B2 | 11/2010 | Dorneich et al. |
| 7,844,347 | B2 | 11/2010 | Brabec |
| 7,849,115 | B2 | 12/2010 | Reiner |
| 7,901,324 | B2 | 3/2011 | Kodama |
| 7,958,002 | B2 | 6/2011 | Bost |
| 7,972,266 | B2 | 7/2011 | Gobeyn et al. |
| 7,988,627 | B2 | 8/2011 | Bagan |
| 8,015,022 | B2 | 9/2011 | Gore |
| 8,018,346 | B2 | 9/2011 | Gottlieb et al. |
| 8,019,121 | B2 | 9/2011 | Marks |
| 8,021,298 | B2 | 9/2011 | Baird |
| 8,024,202 | B2 | 9/2011 | Carroll |
| 8,030,786 | B2 | 10/2011 | Jackson et al. |
| 8,038,615 | B2 | 10/2011 | Gobeyn |
| 8,081,083 | B2 | 12/2011 | Hinterlong |
| 8,083,676 | B2 | 12/2011 | Halliday |
| 8,092,226 | B2 | 1/2012 | Findlay |
| 8,095,641 | B2 | 1/2012 | Aggarwal et al. |
| 8,103,333 | B2 | 1/2012 | Tran |
| 8,179,269 | B2 | 5/2012 | Yanagi et al. |
| 8,180,457 | B2 | 5/2012 | Matos |
| 8,200,323 | B2 | 6/2012 | Dibenedetto et al. |
| 8,203,454 | B2 | 6/2012 | Knight et al. |
| 8,219,184 | B2 | 7/2012 | Stelzer et al. |
| 8,235,895 | B2 | 8/2012 | David |
| 8,308,562 | B2 | 11/2012 | Patton |
| 8,359,231 | B2 | 1/2013 | Fitzpatrick et al. |
| 8,428,962 | B1 | 4/2013 | Brinkley et al. |
| 8,477,039 | B2 | 7/2013 | Gleckler et al. |
| 8,487,456 | B2 | 7/2013 | Donelan et al. |
| 8,597,121 | B2 | 12/2013 | Andres Del Valle |
| 8,597,142 | B2 | 12/2013 | Mayles et al. |
| 8,612,247 | B2 | 12/2013 | Sawano |
| 8,636,670 | B2 | 1/2014 | Ferren et al. |
| 8,704,110 | B2 | 4/2014 | Forshaw et al. |
| 8,738,129 | B2 | 5/2014 | Packer |
| 8,775,196 | B2 | 7/2014 | Simpson et al. |
| 8,956,292 | B2 | 2/2015 | Wekell et al. |
| 9,043,217 | B2 | 5/2015 | Cashman et al. |
| 9,044,172 | B2 | 6/2015 | Baxi et al. |
| 9,364,714 | B2 | 6/2016 | Koduri et al. |
| 2001/0039372 | A1 | 11/2001 | Yasushi et al. |
| 2001/0040591 | A1 | 11/2001 | Abbott et al. |
| 2001/0041845 | A1 | 11/2001 | Kim |

(56) References Cited

U.S. PATENT DOCUMENTS

| | | |
|---|---|---|
| 2001/0042004 A1 | 11/2001 | Taub |
| 2002/0008625 A1 | 1/2002 | Adams et al. |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0214408 A1 | 11/2003 | Grajales et al. |
| 2003/0222440 A1 | 12/2003 | Basir |
| 2003/0226695 A1 | 12/2003 | Mault |
| 2004/0002634 A1 | 1/2004 | Nihtila |
| 2004/0004547 A1 | 1/2004 | Appelt et al. |
| 2004/0015191 A1 | 1/2004 | Otman |
| 2004/0095378 A1 | 5/2004 | Vigue |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0060217 A1 | 3/2005 | Douglas et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0090135 A1 | 4/2006 | Fukuda |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0015422 A1 | 6/2008 | Wessel |
| 2008/0140140 A1 | 6/2008 | Grimley |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Ouwekerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0258921 A1 | 10/2008 | Woo et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |

(56) References Cited

U.S. PATENT DOCUMENTS

| | | |
|---|---|---|
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Guoyi et al. |
| 2010/0312606 A1 | 12/2010 | Gala |
| 2010/0332250 A1 | 12/2010 | Simpson |
| 2011/0030838 A1 | 2/2011 | Turiello |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1* | 6/2011 | Bennett ............... G06Q 50/22 705/2 |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0270135 A1* | 11/2011 | Dooley ............... G16H 50/30 600/595 |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Rotary et al. |
| 2012/0117020 A1 | 5/2012 | Davis et al. |
| 2012/0122430 A1 | 5/2012 | Hutchings et al. |
| 2012/0127157 A1 | 5/2012 | Adler |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1* | 1/2013 | Horseman ............... G16H 40/63 345/633 |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0217350 A1 | 8/2013 | Singh |
| 2013/0226413 A1 | 8/2013 | Cuddihy et al. |
| 2013/0234826 A1 | 9/2013 | Sekiguchi et al. |
| 2013/0243208 A1 | 9/2013 | Fawer |
| 2013/0281798 A1 | 10/2013 | Rau et al. |
| 2013/0282609 A1 | 10/2013 | Au et al. |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2013/0308099 A1 | 11/2013 | Stack |
| 2013/0331993 A1 | 12/2013 | Detsch et al. |
| 2013/0334851 A1 | 12/2013 | Hoell et al. |
| 2014/0041105 A1 | 2/2014 | Zemlak |
| 2014/0067001 A1 | 3/2014 | Schwibner et al. |
| 2014/0100464 A1 | 4/2014 | Kaleal et al. |
| 2014/0107718 A1 | 4/2014 | Foote |
| 2014/0129401 A1 | 5/2014 | Kruz et al. |
| 2014/0156259 A1 | 6/2014 | Dolan et al. |
| 2014/0172461 A1 | 6/2014 | Rogers |
| 2014/0222095 A1 | 8/2014 | Einy |
| 2014/0304020 A1* | 10/2014 | Casper ............... G06Q 10/06311 705/7.17 |
| 2014/0317914 A1 | 10/2014 | Shaker |
| 2014/0372133 A1* | 12/2014 | Austrum ............... G06F 19/3475 705/2 |
| 2015/0025928 A1 | 1/2015 | Kang et al. |
| 2015/0050623 A1 | 2/2015 | Falash et al. |
| 2015/0134347 A1 | 5/2015 | Faurie et al. |
| 2015/0199494 A1 | 7/2015 | Koduri et al. |
| 2015/0222096 A1 | 8/2015 | Nakayama |
| 2015/0338265 A1 | 11/2015 | Carreel et al. |
| 2015/0375028 A1 | 12/2015 | Oteman et al. |
| 2016/0132046 A1 | 5/2016 | Beoughter et al. |
| 2016/0321935 A1 | 11/2016 | Mohler et al. |
| 2017/0245806 A1 | 8/2017 | Elhawary et al. |

(56) References Cited

U.S. PATENT DOCUMENTS

| | | |
|---|---|---|
| 2017/0270481 A1 | 9/2017 | Morgenthau et al. |
| 2017/0290516 A1 | 10/2017 | Nguyen et al. |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |
| EP | 1407713 B1 | 9/2008 |
| EP | 2151355 A1 | 2/2010 |
| EP | 2248461 A2 | 11/2010 |
| EP | 2924674 A1 | 9/2015 |
| JP | 05049603 A | 3/1993 |
| JP | H07204168 A | 8/1995 |
| JP | H10283150 A | 10/1998 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001236141 A | 8/2001 |
| JP | 2001356849 A | 12/2001 |
| JP | 2002065630 A | 3/2002 |
| JP | 2002109061 A | 4/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003235813 A | 8/2003 |
| JP | 2003247991 A | 9/2003 |
| JP | 2003256578 A | 9/2003 |
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2006239157 A | 9/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 2001028416 A1 | 4/2001 |
| WO | 2001086403 A2 | 11/2001 |
| WO | 03077110 A2 | 9/2003 |
| WO | 2005064447 A2 | 7/2005 |
| WO | 2006022465 A2 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | WO2014023422 A1 | 2/2014 |

OTHER PUBLICATIONS

"Biofeedback—MayoClinic.com", retrieved from <http://www.mayoclinic.com/health/biofeedback/MY01072>, May 7, 2012. (pp. 1-2).

"Cardinus Risk Management | Ergonomic & DSE Risk Assessments", retrieved from <http://www.cardinus.com/>, Sep. 12, 2012. (pp. 1-2).

"Chronic diseases and health promotion" Centers for Disease Control and Prevention, 2011, available at the websote: http://www.cdc.gov/chronicdisease/overview; pp. 1-3.

"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).

"Electroencephalography (EEG)", retieved from <http://www.emedicinehealth.com/script/main/art.asp?articlekey-59319&pf=3&page=1>, Jun. 11, 2012. (pp. 1-4).

"Emotiv|EEG System|Electroencephalography", retrieved from <www.emotiv.com/index.asp>, Jun. 11, 2012. (pp. 1-2).

"EmotivEPOC Software Devlopment Kit", retrieved from <www.emotiv.com/store/hardware/epoc-bci-eeg/developer-neuro-jheadset/>, Jun. 11, 2012. (pp. 1-2).

"Kinect—Xbox.com", retrieved from <http://www.xbox.com/en-US/kinect>, Jun. 11, 2012. (pp. 1-3).

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Chapman, Larry S. MPH, "Meta-evaluation of Worksite Health Promotion Economic Return Studies: 2005 Update", Jul./Aug. 2005. (pp. 1-11).

Collins English Dictionary, definition of mat, 2008, retrieved at www.collinsdictionary.com.

Duke, Sean, "A 'smartphone' based defibrillator" Science Spin, Jan. 11, 2011: pp. 1-2.

Dux, Paul E., and René Marois. "The attentional blink: A review of data and theory." Attention, Perception, & Psychophysics 71.8 (2009): 1683-1700.

Dux, Paul E., et al. "Training improves multitasking performance by increasing the speed of information processing in human prefrontal cortex." Neuron 63.1 (2009): 127-138.

Edington, D. W., "Emerging research: a view from one research centre", American Journal of Health Promotion, 15(5), May/Jun. 2001, pp. 341-349.

Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.

"Electric double-layer capacitor" Wikipedia; available at the website: http://en.wikipedia.org/wiki/electric_double-layer_capacitor as of Dec. 5, 2014; pp. 1-8.

Elliott, Stephen N., et al. "Cognitive load theory: Instruction-based research with applications for designing tests." Proceedings of the National Association of School Psychologists' Annual Convention, Boston, MA, Feb.. vol. 24. 2009.

EPO: "Notice from the European Patent Office dated Oct. 1, 2007 concerning business methods" Official Journal EPO, vol. 30, No. 11, Nov. 1, 2007, pp. 592-593, XP007905525.

Fadel, Charles, et al. "Multimodal Learning Through Media: What the Research Says" Cisco Systems, Inc. (2008) pp. 1-24.

Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.

Filmer, Hannah L., et al. "Disrupting prefrontal cortex prevents performance gains from sensory-motor training." The Journal of Neuroscience 33.47 (2013): 18654-18660.

(56) References Cited

OTHER PUBLICATIONS

Fougnie, Daryl, and René Marois. "What limits working memory capacity? Evidence for modality-specific sources to the simultaneous storage of visual and auditory arrays." Journal of Experimental Psychology: Learning, Memory, and Cognition 37.6 (2011): 132.
Georgia Tech, "Prowess Proactive Wellness Environment Support System", Dec. 12, 2009, pp. 1-27, www.hsi.gatech.edu/onsitecenter/index.php/PROWESS.
Goetzel et al. "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.
Goetzel et al. 'Estimating the Return-on-Investment From Changes in Employee Health Risks on TheDow Chemical Company's Health Care Costs'—J Occup Environ Med. (JOEM) vol. 47, No. 8, dated Aug. 2005; pp. 759-768.
Goetzel et al. 'Health, Absence, Disability, and Presenteeism Cost Estimates of Certain Physical and MentalHealth Conditions Affecting U.S. Employers'—J Occup Environ Med. (JOEM) vol. 46, No. 4, dated Apr. 2004; pp. 398-412.
Goetzel et al. 'Second-Year Results of an Obesity Prevention Program at TheDow Chemical Company'—J Occup Environ Med. (JOEM) vol. 52, No. 3, dated Mar. 2010; pp. 291-302.
Goetzel et al. 'The Health and Productivity Cost Burden of the "Top 10" Physical and Mental HealthConditions Affecting Six Large U.S. Employers in 1999'—J Occup Environ Med. (JOEM) vol. 45, No. 1, dated Jan. 2003; pp. 5-14.
Goetzel et al. 'The Long-Term Impact of Johnson & Johnson's Health & Wellness Program onEmployee Health Risks'—J Occup Environ Med. (JOEM) vol. 44, No. 5, dated May 2002; pp. 417-424.
Goetzel et al. 'The Workforce Wellness Index'—J Occup Environ Med. (JOEM) vol. 55, No. 3, dated Mar. 2013; pp. 272-279.
Goetzel et al. The Predictive Validity of the HERO Scorecard in Determining Future Health Care Cost and Risk Trends—J Occup Environ Med. (JOEM) vol. 56, No. 2, dated Feb. 2014; pp. 136-144.
Health/Medical Writers eHealthcareWorld 2000. (May 1). MyDailyHealth.com (pp. 1-3).
Hemp, P., "Presenteeism: At Work—But Out of It", Harvard Business Review, Oct. 2004, pp. 49-58.
Horseman, S. J., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.
Quick, James Campbell, et al. "Executive health: Building strength, managing risks" Academy of Management Executive, May 2000, vol. 14, No. 2, pp. 33-45.
Surkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart; pp. 1-5.
"40 Best Companies for Leaders—2014" Chief Executive, available as of Dec. 13, 2015 at the website: http://chiefexecutive.net/40-best-companies-for-leaders-2014/; pp. 1-3.
Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp. 1-4.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the website: http://journal.frontiersin.org/article/10.3389/fnhum.2014.00792/full; pp. 1-9.
Ovans, Andrea; "What Resilience Means, and Why it Matters" Harvard Business Review Jan. 5, 2015; pp. 1-6.
"Qlik Technology Partners" available as of Oct. 2, 2015 at the website: http://www.qlik.com/us/partners/technology-partners; pp. 1-21.
Lamkin, Paul; "The best VR headsets: Oculust Rift, PlayStation VR, Gear VR, HTC Vive . . . virtual reality is back baby" Sep. 16, 2015; available as of Oct. 2, 2015 at the website: http://www.wearable.com/headgear/the-best-ar-and-vr-headsets; pp. 1-18.
Hill, Jr., Randall W.; "How Virtual Humans Can Build Better Leaders" Harvard Business Review Jul. 25, 2014; pp. 1-4.
"Veeva Systems and Zinc Ahead Join Forces" available as of Oct. 2, 2015 at the website: http://www.veeva.com; pp. 1-6.
Ready, Douglas A., et al.; "Are You a High Potential?" Harvard Business Review Jun. 2010; pp. 1-13.
Horseman, Samantha, et al.; "Gamefication of Health, Safety and the Environment (HSE): An Avatarial Solution" American Society of Safety Engineers 11th Professional Development Conference & Exhibition, Bahrain, Mar. 2014; pp. 1-10.
Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-ventures-and-eric-schmidt-urban-engines-wants-to-solve-urban-congestion-using-data-intellince; pp. 1-7.
Agarabi, Mina, et al., "A sEMG-based Method for Assessing the Design of Computer Mice" 26th Annual International Conference of the IEEE EMBS, Sep. 1-5, 2004; pp. 2450-2453.
Robertini, Nadia, et al., "Capture of Arm-Muscle Deformations using a Depth-Camera" 10 European Conference on Visual Media Production, London, UK, Nov. 6-7, 2013; pp. 1-10.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Hacker, et al. "Representation and visualization of variability in a 3D anatomical atlas using the kidney as an example." Medical Imaging. International Society for Optics and Photonics, 2006. XP055342027 (pp. 1-7).
International Search Report and Written Opinion for International Application No. PCT/US2016/064518; International Filing Date Dec. 2, 2016; Report dated Feb. 17, 2017; (SA5302/PCT); (pp. 1-16).
International Search Report and Written Opinion for International Application No. PCT/US2016/065042; International Filing Date Dec. 6, 2016; Report dated Mar. 17, 2017; (SA5400/PCT); pp. 1-15.
International Search Report and Written Opinion for International PCT application PCT/US2016/064520; International Filing Date Dec. 2, 2016; Report dated Mar. 27, 2017; (SA5352/PCT); pp. 1-10.
International Search Report and Written Opinion for International PCT application PCT/US2016/064521; International Filing Date Dec. 2, 2016; Report dated Mar. 20, 2017; (SA5323/PCT); pp. 1-17.
Stephens: "I am 38. My heart is only 33, but my lungs are aged 52. Why?" Mail Online; http://www. dailymail.co.uk/health/article-1249009/I-38-My-heart-only33-lungs-aged-52-Why.html; retrieved on Feb. 3, 2017; XP055342045 (pp. 1-7).
Index for "Micro-NanoMechatronics and Human Science (MHS), 2010 International Symposium Nov. 2010", retrieved from <http://ieeexplore.ieee.org/xpl/mostRecentIssue.jsp?punumber=5658189>Ma 7, 2012. (pp. 1-5).
International Preliminary Report on Patentability for International Application No. PCT/US2012/045395 (SA741PCT), dated Jan. 7, 2014. (pp. 1-12).
International Preliminary Report on Patentability for International Application No. PCT/US2012/045401 (SA5050PCT) dated Jan. 7, 2014. (pp. 1-9).
International Preliminary Report on Patentability for International Application No. PCT/US2012/045407 (SA5051PCT) dated Jan. 7, 2014. (pp. 1-8).
International Preliminary Report on Patentability for International Application No. PCT/US2012/045410 (SA5052PCT) dated Jan. 7, 2014. (pp. 1-8).

(56) References Cited

OTHER PUBLICATIONS

International Preliminary Report on Patentability for International Application No. PCT/US2012/045414 (SA5053PCT) dated Jan. 7, 2014. (pp. 1-8).
International Preliminary Report on Patentability for International Application No. PCT/US2012/045419 (SA5054PCT) dated Jan. 7, 2014. (pp. 1-11).
International Preliminary Report on Patentability for International Application No. PCT/US2012/045427 (SA5055PCT) dated Jan. 7, 2014. (pp. 1-10).
International Preliminary Report on Patentability for International Application No. PCT/US2012/045435 (SA5059PCT) dated Jan. 7, 2014. (pp. 1-10).
International Preliminary Report on Patentability for International Application No. PCT/US2012/045442 (SA5076PCT) dated Jan. 7, 2014. (pp. 1-10).
International Preliminary Report on Patentability for International Application No. PCT/US2012/045447 (SA5075PCT) dated Jan. 7, 2014. (pp. 1-8).
International Preliminary Report on Patentability for International Application No. PCT/US2012/045452 (SA5074PCT) dated Jan. 7, 2014. (pp. 1-9).
International Search Report & Written Opinion for International Application No. PCT/US2012/045401, dated Feb. 5, 2013. (pp. 1-13).
International Search Report & Written Opinion for International Application No. PCT/US2012/045407, dated Jan. 23, 2013. (pp. 1-15).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045447, dated Jan. 18, 2013. (pp. 1-12).
International Search Report and Written Opinion for International Application No. PCT/US2004/045442, dated Nov. 7, 2012, pp. 1-14.
International Search Report and Written Opinion for International Application No. PCT/US2012/045395, dated Dec. 3, 2012, pp. 1-16.
International Search Report and Written Opinion for International Application No. PCT/US2012/045419, dated Dec. 6, 2012, pp. 1-16.
International Search Report and Written Opinion for International Application No. PCT/US2012/045427, dated Dec. 3, 2012, pp. 1-14.
International Search Report and Written Opinion for International Application No. PCT/US2012/045452, dated Dec. 3, 2012, pp. 1-14.
International Search Report and Written Opinion for PCT/US2014/056427 (SA5169PCT) dated Apr. 22, 2015.
International Search Report and Written Opinion for PCT/US2014/069498 (SA5203PCT) dated Apr. 1, 2015.
Ivanoff, Jason, Philip Branning, and René Marois. "fMRI evidence for a dual process account of the speed-accuracy tradeoff in decision-making." PLoS one 3.7 (2008): e2635. pp. 1-14.
Jamison, Dean T., et al.; "The World Health Report 1999" World Health Organization, WHO Library Cataloguing in Publication Data, 1999; pp. 1-136.
Johns, G., "Presenteeism in the Workplace: A review and research agenda", Journal of Organizational Behavior, Jul. 31, 2009, pp. 519-542.
Kelly et al. The Novartis Health Index: A Method for Valuing the Economic Impact of Risk Reduction in a Workforce'—J Occup Environ Med. (JOEM) vol. 52, No. 5, dated May 2010; pp. 528-535.
Knikou, Maria. "The H-reflex as a probe: pathways and pitfalls." Journal of neuroscience methods 171.1 (2008): 1-12.
Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Marois, René, and Jason Ivanoff. "Capacity limits of information processing in the brain." Trends in cognitive sciences 9.6 (2005): 296-305.
Moreno, Roxana, and Alfred Valdez. "Cognitive load and learning effects of having students organize pictures and words in multimedia environments: The role of student interactivity and feedback." Educational Technology Research and Development 53.3 (2005.
Moreno, Roxana, and Richard Mayer. "Interactive multimodal learning environments." Educational Psychology Review 19.3 (2007): 309-326.
Moreno, Roxana. "Learning in high-tech and multimedia environments." Current directions in psychological science 15.2 (2006): 63-67.
Nintendo of America Inc., Wii Balance Board Operations Manual, 2008, pp. 1-10.
Nintendo of America Inc., Wii Fit Instruction Booklet, 2008, pp. 1-28.
Nintendo Wii Fit, https://www.youtube.com/watch?v=-Taruqvk30E, May 11, 2008.
Priya, S., "Advances in Energy Harvesting Using Low Profile Piezoelectric Transducers", Materials Science & Engineering, Springer, Mar. 2007, pp. 165-182.
Prochaska et al. 'The Well-Being Assessment for Productivity'—J Occup Environ Med. (JOEM) vol. 53, No. 7, dated Jul. 2011; pp. 735-768.
Raybourn, Elaine M., et al. "Adaptive thinking & leadership simulation game training for special forces officers." ITSEC 2005 Proceedings, Interservice/Industry Training, Simulation and Education Conference Proceedings, Nov. 2005.
Reidel, J.E., Baase, C., "The effect of disease prevention & health promotion on worksite productivity: a literature review", American Journal of Health Promotion, 15:3, Jan./Feb. 2001, pp. 167-191, 243.
Rimor, Rikki, Yigal Rosen, and Kefaya Naser. "Complexity of social interactions in collaborative learning: The case of online database environment." Interdisciplinary Journal of E-Learning and Learning Objects 6.1 (2010): 355-365.
Roberts, R.O.,Bergstralh, E.J., Schmidt, L, Jacobsoen,S.J., "Comparison of Self Reported and Medical Record Health Care Utilization Measures", Journal of Clinical Epidemiology, 49:9, Feb. 1996, pp. 989-995.
Rosen, Yigal. "The effects of an animation-based on-line learning environment on transfer of knowledge and on motivation for science and technology learning." Journal of Educational Computing Research 40.4 (2009): 451-467.
Simmonds, Bethany, et al. "Objectively assessed physical activity and subsequent health service use of UK adults aged 70 and over: A four to five year follow up study." PloS one 9.5 (2014): e97676.
Slater et al., "Taking Steps: The Influence of a Walking Technique on Presence in Virtual Reality", ACM Transactions on Computer-Human Interaction, Sep. 1995, pp. 201-219, vol. 2 No. 3.
Sullivan 'Making the Business Case for Health and Productivity Management'—J Occup Environ Med. (JOEM) vol. 46, No. 6 suppl, dated Jun. 2004; pp. S56-S61.
The American Heritage Dictionary of the English Language, definition of planar, 2000.
The constitution of the World Health Organization, World Health Organization, WHO Chronicle, 1947, pp. 1-202.
Wang, Xiaoning. "An Empirical Study of Optimizing Cognitive Load in Multimedia Integrated English Teaching." Studies in Literature and Language 9.3 (2014): 70.

(56) References Cited

OTHER PUBLICATIONS

Withings, The Internet connected Body Scale, retrieved with the Wayback Machine using link at www.withings.com, Jan. 11, 2010.
World Economic Forum 'The Workplace Wellness Alliance-Making the Right Investment: Employee Health and the Power of Metrics' dated Jan. 2013; pp. 1-35.
"Making a Difference", World Health Organisation, Geneva: WHO, 1999, pp. 1-136.
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Murray Hill, WellMed Team to Offer Next Generation Online Preventive Health Services" ProQuest, PR Newswire, New York, Nov. 3, 1999, 3 pages.
"National Health Expenditure Data", Centers for Medicare & Medicaid Services, available at: <https://www.cms.gov/Research-Statistics-Data-and-Systems/Statistics-Trends-and-Reports/NationalHealthExpendData/index.html>, accessed Nov. 18, 2013, pp. 1-2.
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"Research programs—Philips Research", retrieved from <http://www.research.philips.com/programs/index.html>, May 7, 2012. (pp. 1-2).
"RJL Systems, Products", retrieved from <http://www.rjlsystems.com/products.shtml>, May 7, 2012. (p. 1).
"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo In Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, 1 page, XP002456414.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Aldana, S., "Financial Impact of health promotion programs: a comprehensive review of the literature", American Journal of Health Promotion,155, 2001, pp. 296-320.
Aldana, S., Merrill, R., Price, K., Hardy, A., and Hager, R., "Financial impact of a comprehensive multi-site worksite health promotion program", Preventive Medicine, 40, Jul. 2004, pp. 131-137.
Alfredo Vazquez Carazo, "Novel Piezoelectric Transducers for High Voltage Measurements", Jan. 2000, pp. 1-277.
Asplund, Christopher L., et al. "A central role for the lateral prefrontal cortex in goal-directed and stimulus-driven attention." Nature neuroscience 13.4 (2010): 507-512.
Asplund, Christopher L., et al. "The attentional blink reveals the probabilistic nature of discrete conscious perception." Psychological science 25.3 (2014): 824-831.
Baicker, K., Cutler, D., Song, Z., "Worksite wellness programs can generate savings", Health Affairs 29(2), Jan. 2010, pp. 1-8.
Bed-Check Co., Bed-Check Monitoring Systems, 2006, pp. 1-8.
Berger et al. 'Investing in Healthy Human Capital'—J Occup Environ Med. (JOEM) vol. 45, No. 12, dated Dec. 2003; pp. 1213-1225.
Berry, Leonard et al., "What's the Hard Return on Employee Wellness Programs?", Harvard Business Review, Dec. 2010. (pp. 1-10).
Borah, J. "Conceptual modeling-The missing link of simulation development." Proceedings of the 2002 Spring Simulation Conference. 2002. AEgis Technologies Group; pp. 1-7.
Brown et al, "Prowess Proactive Wellness Environment Support System", Dec. 10, 2009, pp. 1-19, www.hsi.gatech.edu/onsitecenter/index.php/PROWESS.
Campbell et al., "The Rise of People-Centric Sensing", IEEE Computer Society, 2008, pp. 12-21, IEEE.
International Search Report and Written Opinion for related PCT application PCT/US2018/064161 (SA5721) dated Feb. 28, 2019; pp. 1-13.

* cited by examiner

| | BMI | Fat Percent | | Systolic BP | | Diastolic BP | | Activity Level |
|---|---|---|---|---|---|---|---|---|
| | | Male | Female | High | Low | High | Low | |
| No Risk | 18-25 | 14%-20% | 23%-25% | 91-139 | 61-80 | 70-90 | 41-60 | Standard |
| 1 Risk | 25-27 | ≤5% or 21%-29% | ≤12% or 26%-34% | 140-179 | 61-90 | 90-109 | 41-60 | |
| 2 Risks | 28-29 | 30%+ | 35%+ | 180-209 | 51-60 | 110-119 | 34-40 | |
| 3 Risks | 30-34 | | | 210+ | ≤50 | 120+ | ≤33 | |
| 4 Risks | 35-40 | | | | | | | |
| 5 Risks | 40+ | | | | | | | |
| *Risk Avoidance | | 6%-13% | 13%-22% | | | | | Athletic |

| | Physiological Score | | | | | | | | |
|---|---|---|---|---|---|---|---|---|---|
| Date | Low (0-2 Health Risk) | | | Medium (2-3 Health Risk) | | | High (≥4 Health Risk) | | |
| | Blood Pressure | Resting Heart Rate | Blood Glucose | Weight | Body Mass Index | Fat % | Total Body Water | Medical Risk | Health Risk | Additional Follow Up |
| 9/9/2015 | 156/89 | 116 | 88 | 75.6KG | 29.5 | 30.10% | 38.6KG | Healthy | Low | |
| | | | | | | | | | | |
| | | | | | | | | | | |
| | | | | | | | | | | |

FIG. 16A

| | Performance Test/30 | | | | | | |
|---|---|---|---|---|---|---|---|
| Date | Balance | Hand Eye Coordination | Reaction Test | Lower Body Quadriceps Strength / Muscular Endurance | Trunk Flexibility | Core Strength | Total Score |
| 9/9/2015 | 2 | 1 | 4 | 5 | 4 | 5 | 21 |
| | | | | | | | |
| | | | | | | | |
| | | | | | | | |

FIG. 16B

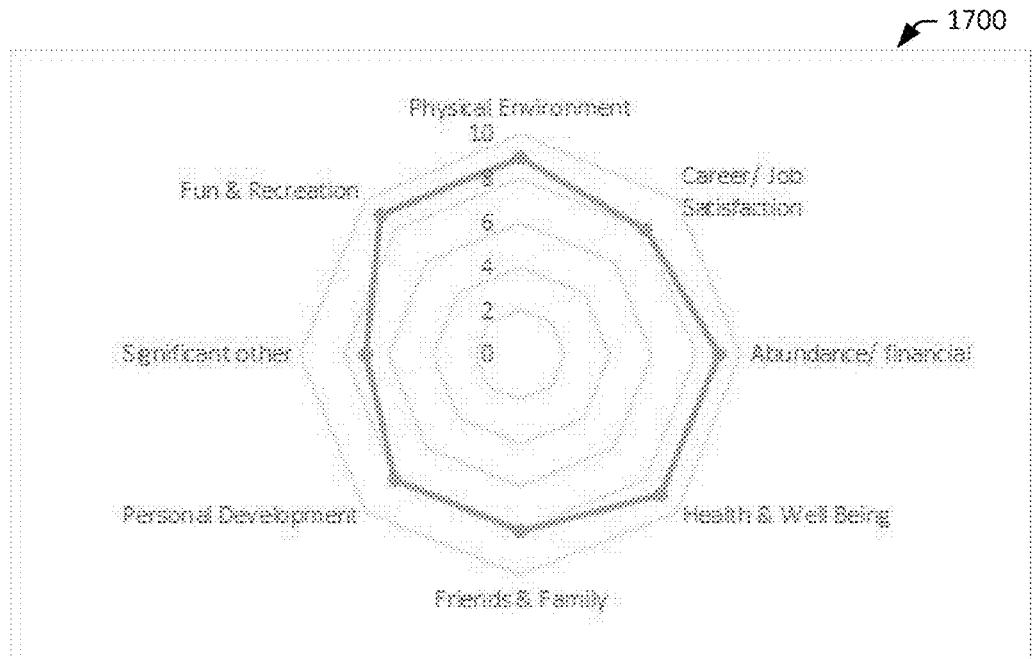

FIG. 17

SYSTEMS AND METHODS FOR ACQUIRING AND EMPLOYING RESILIENCY DATA FOR LEADERSHIP DEVELOPMENT

FIELD OF INVENTION

The present invention relates generally to organizational leadership programs and more particularly to systems and methods for acquiring and employing resiliency data for organizational leadership development programs.

BACKGROUND OF THE INVENTION

Organizations (e.g., companies) are often looking for cost-effective and efficient methods to improve employee safety, health and wellness. In some instances, organizations employ workplace wellness programs to facilitate healthy and positive lifestyles. A workplace wellness program can include, for example, activities or organizational policies designed to support healthy behavior in the workplace and improve the health of employees and their families. Wellness programs can involve a variety of activities such as health fairs, health education classes, physical activity classes, medical/health screenings, health coaching, weight management programs, injury prevention programs, fitness programs, and the like. Wellness programs can also involve providing information and facilities to support healthy lifestyle including, such as health literature, on-site fitness facilities, on-site medical clinics, and so forth. It is believed that workplace wellness programs can lead to a "culture of health" within a workplace that can help to prevent injury and sickness, and provide a positive impact on workforce health behaviors, performance, and work factors. For example, workplace wellness programs are often associated with reductions of health risks (e.g., health risk associated with body mass index (BMI), blood pressure (BP), and body fat percentage) and improved work factors (e.g., improved job satisfaction, stress management, work engagement, and productivity). Moreover, workplace wellness programs can provide a positive financial benefit for organizations. For example, a company may see a reduction in medical costs due to medical risks and conditions that are avoided as a result of a workplace wellness program, as well as revenue increases attributable to improved work factors (e.g., increases productivity due to improved health, reduced stress, and the like).

In addition to looking for cost-effective and efficient methods to improve employee safety, health and wellness, organizations are often looking for ways to develop leadership within the organization. This can include, for example, identifying, developing, and promoting employees that exhibit leadership qualities. Developing leaders can be of particular importance in large workforces. However, it can be difficult to identify persons that exhibit desired leadership qualities, especially in large workforce with a relatively large number of leadership candidates.

SUMMARY OF THE INVENTION

Applicants have recognized several shortcomings of existing systems and methods for developing leadership within organizations and, in view of these shortcomings, has recognized the need for system and methods that can effectively identify, develop, and promote employees that exhibit leadership qualities. Applicants have recognized that although existing systems and methods for developing leadership within organizations, such as annual evaluations, provide some mechanisms for identifying, developing, and promoting leaders, they may not take advantage of numerous factors that can provide significant insight into identifying, developing and promoting leadership within a workforce. For example, traditional systems and methods have failed to take into account the impact that an employee's health can have on her/his ability to lead effectively. This has been confirmed by research indicating that healthy employees are more likely to be more effective leaders. For example, certain studies have shown that people generally favor leaders that look healthier. (See, e.g., Burkus, D., For Leaders, Looking Healthy Matters More than Looking Smart. *Harvard Business Review.* January 2015. available at <https://hbr.org/2015/01/for-leaders-looking-healthy-matters-more-than-looking-smart>; Spisak et al., A face for all seasons: Searching for context-specific leadership traits and discovering a general preference for perceived health. *Front. Hum. Neurosci.,* November, 2014. available at <http://journal.frontiersin.org/article/10.3389/fnhum.2014.00792/abstract>; and Owens, A. (2015). What Resilience Means, and Why It Matters. *Harvard Business Review,* January 2015. at <https://hbr.org/2015/01/what-resilience-means-and-why-it-matters&cm_sp=Article-_-Links-_-Top%20of%20-Page%20Recirculation>). In particular, some studies for selection of leadership candidates have shown that 69% of participants selected leadership candidates having healthy looking-faces over leadership candidates having less healthy-looking faces. Such studies have also determined that a relatively healthy-looking leader may have a better chance of gaining sufficient levels of followership and, thus, may be more successful in initiating change with an organization. Further, a potential leader who looks relatively less healthy may be over-looked even if they are better suited for the job.

Consistent with these findings, Applicants have recognized the implications of healthy and unhealthy lifestyles on leadership within an organization. For example, Applicants have recognized that leadership can be identified and developed using a more holistic model which takes into account health, as well as more traditional factors, such as employee performance. In an effort to expand on these findings, Applicants have developed systems and method for developing leadership within an organization which take into account various health factors. In some embodiments, the systems and method employ a resilience algorithm that takes into account various health factors to arrive at a resiliency score for employees. As described herein, such as resiliency score may be used to rank employees relative to one another. In some embodiments, such as ranking can be used to identify and select potential leaders from a group of candidate employees. For example, candidate employees having relatively high resiliency scores may be automatically recommended or selected for promotion into a leadership position. In some embodiments, such as resiliency score can be used to encourage employee participation in leadership development programs. For example, rankings of candidate employees may be made available to the candidate employees so that they are challenged to improve their rankings in a competitive, game-like atmosphere. As described herein, various embodiments can include dashboards or other graphical user interfaces (GUI) that communicate leadership information to employees and/or employers. For example, employee dashboards may help to inform and challenge employees to improve their scores, as well as provided helpful tips and suggestions for developing their health and leadership. Employer dashboards may help to inform employers about the development of individual employees and/or groups of employees.

Also provided are novel systems and method for acquiring the information that can be used to assess the development of employee leadership. For example, some embodiments may employ leadership testing centers (or "pop-up" clinics) that can be used to acquire employee resiliency data. In some embodiments, these pop-up clinics can provide for submission of employee general health information, and/or conducting various health tests, such as health status tests and functional performance tests. Such leadership testing centers may employ various data acquisition devices, such as interactive surveys, health-sensing chairs, health-sensing caps, virtual reality (VR) systems, and/or the like. In some embodiments, a VR system can be employed to conduct virtual functional performance tests for an employee. For example, the VR system can include an augmented VR headset that is worn by the employee and displays scenes for virtual reaction tests (e.g., quickly catching a falling object), virtual coordination tests (e.g., catching multiple objects in flight), and or the like. In some embodiments, the leadership testing centers can be used to acquire baseline resiliency data for candidate employees, and this baseline data can be supplemented with other resiliency data, such as that acquired during subsequent employee visits (e.g., weekly visits) to the leadership testing centers, or during the course of work (e.g., via real-time health monitoring system provided in the candidate employee's work environment).

Such systems and methods for developing leadership can provide an integrated leadership training solution that develops mindful, engaged, and resilient leaders, that, in turn, creates an energized, satisfied, and high performing workforce. Further, the systems can encourage candidate employees to resist the temptation of focusing on career or health goals, or separating the two in her/his mind, and can, instead encourage the employee to think holistically. If an employee is looking to get a promotion, she/he may recognize that health matters just as much (if not more) than the experience and knowledge. This can provide a well-rounded organization with a high return on investment through retention and attraction of talent, enhancement of organizational health, and positioning as an employer of choice. Moreover, such an investment in healthy, engaged, and high performing workforce can provide a competitive advantage for the organization.

Provided in some embodiments is an employee management system. The system may include an employee resiliency data acquisition system and an employee leadership assessment system. The employee resiliency data acquisition system may include a terminal adapted to acquire health information for an employee via an interactive health survey; one or more health sensor systems adapted to acquire health status data for the employee; an augmented virtual reality (AVR) headset adapted to be worn about the head of the employee, the AVR headset being adapted to present, for viewing by the employee, a functional performance test including a virtual scene including one or more virtual objects for the employee to interact with, and the AVR headset being adapted to generate functional performance test data for the employee that is indicative of the interactions of the employee with the one or more virtual objects. The employee leadership assessment system may be communicatively coupled to the employee resiliency data acquisition system via a communications network, the employee leadership assessment system including a non-transitory computer readable storage medium including program instructions stored thereon that are executable by one or more processors to cause: receiving, from the employee resiliency data acquisition system, a set of resiliency data for the employee, the set of resiliency data corresponding to the health information for the employee, the health status data for the employee, and the functional performance test data for the employee; determining a resiliency score for the employee based at least in part on the set of resiliency data, the resiliency score indicating a change in a cost associated with the employee over a given period of time; determining that the employee is recommended for a promotion to a leadership position within an organization based at least in part on the resiliency score; determining a ranking of the employee relative to other employees within the organization based at least in part on the resiliency score; serving, to a first device for display to the employee, an employee leadership review dashboard including: an indication of the resiliency score for the employee; and an indication of the ranking of the employee relative to the other employees; and serving, to a second device for display to an employer, an employer leadership review dashboard including: an indication of the resiliency score for the employee; an indication that the employee is recommended for the promotion to the leadership position within the organization; and an indication of the ranking of the employee relative to the other employees.

In certain embodiments, the functional performance test includes a reaction-drop test and the virtual scene includes a virtual object appearing to fall in the field of view (FOV) of the employee, and wherein the employee is tasked with catching the virtual object. In some embodiments, the functional performance test includes a coordination-catch test and the virtual scene includes multiple virtual objects appearing to move toward the employee in the field of view (FOV) of the employee, and wherein the employee is tasked with catching the one or more virtual objects.

In certain embodiments, the one or more health sensor systems include a chair including one or more health sensors integrated into at least one of a seat bottom, a seat back, an arm rest and a headrest of the chair, wherein the one or more health sensors are adapted to contact the employee when the employee is seated in the chair. In some embodiments, the one or more health sensor systems include a cap adapted to be worn by the employee, and wherein the cap includes one or more electroencephalogram (EEG) sensors located in an interior of the cap such that the EEG sensors contact at least a portion of the scalp of the employee while the employee is wearing the cap. In certain embodiments, the one or more health sensor systems include one or more electroencephalogram (EEG) sensors located in an interior of the AVR headset such that the EEG sensors contact at least a portion of the scalp of the employee while the employee is wearing the AVR headset.

In some embodiments, the set of resiliency data is associated with a first time, and wherein the program instructions stored thereon that are executable by one or more processors to cause: receiving, from the employee resiliency data acquisition system, a second set of resiliency data for the employee, the second resiliency data corresponding to health information for the employee at a second time, health status data for the employee at the second time, and functional performance test data for the employee at the second time, wherein the resiliency score is determined as a difference between a first value determined based on the set of resiliency data associated with the first time, and a second value determined based on the second set of resiliency data associated with the second time.

In certain embodiments, the employee is a participant in an employee leadership program, and the employer leadership review dashboard includes a spider diagram including a first web indicative of a set of scores for the employee in one or more life areas, and a second web indicative of a set of scores for a group of employees participating in employee leadership program in the one or more life areas. In some embodiments, the employee leadership review dashboard includes a challenge link corresponding to a life area, and wherein the employee leadership review dashboard is adapted to, in response to selection of the challenge link, display content suggestions for the employee to improve in the life area. In certain embodiments, the employee leadership review dashboard includes a challenge link corresponding to a life area, and wherein the program instructions are further executable by the one or more processors to cause: automatically scheduling, in response to selection of the challenge link, one or more activities for the employee that are expected to improve the life area for the employee. In some embodiments, automatically scheduling the one or more activities for the employee includes automatically adding one or more calendar events for the one or more activities to an electronic calendar for the employee.

In certain embodiments, the program instructions are further executable by the one or more processors to cause: determining a score for the employee in a life area based at least in part on the set of resiliency data; determining whether the score for the employee in the life area satisfies a life area score threshold; and in response to determine that the score for the employee in the life area does not satisfy the life area score threshold, automatically scheduling one or more activities for the employee that are expected to improve the life area for the employee.

Provided in some embodiments is a method that includes: acquiring a set of resiliency data for an employee, the resiliency data including: health information for the employee acquired via an interactive health survey; health status data for the employee acquired via one or more health sensor systems; and functional performance test data for the employee, the functional performance test data acquired via a virtual performance test conducted using an augmented virtual reality (AVR) headset worn about the head of the employee and presenting, for viewing by the employee, a functional performance test including a virtual scene including one or more virtual objects for the employee to interact with, and the functional performance test data for the employee being indicative of the interactions of the employee with the one or more virtual objects; determining a resiliency score for the employee based at least in part on the set of resiliency data, the resiliency score indicating a change in a cost associated with the employee over a given period of time; determining that the employee is recommended for a promotion to a leadership position within an organization based at least in part on the resiliency score; determining a ranking of the employee relative to other employees within the organization based at least in part on the resiliency score; and serving, to a first device for display to the employee, an employee leadership review dashboard including: an indication of the resiliency score for the employee; and an indication of the ranking of the employee relative to the other employees.

In certain embodiments, the method includes serving, to a second device for display to an employer, an employer leadership review dashboard including: an indication of the resiliency score for the employee; an indication that the employee is recommended for the promotion to the leadership position within the organization; and an indication of the ranking of the employee relative to the other employees.

In some embodiments, the set of resiliency data is associated with a first time, and the method further includes: receiving a second set of resiliency data for the employee, the second resiliency data corresponding to health information for the employee at a second time, health status data for the employee at the second time, and functional performance test data for the employee at the second time, wherein the resiliency score is determined as a difference between a first value determined based on the set of resiliency data associated with the first time, and a second value determined based on the second set of resiliency data associated with the second time.

In certain embodiments, the method includes determining a score for the employee in a life area based at least in part on the set of resiliency data; determining whether the score for the employee in the life area satisfies a life area score threshold; and in response to determine that the score for the employee in the life area does not satisfy the life area score threshold, automatically scheduling one or more activities for the employee that are expected to improve the life area for the employee.

Provided in some embodiments is a non-transitory computer readable storage medium including program instructions stored thereon that are executable by one or more processors to cause: acquiring a set of resiliency data for an employee, the resiliency data including: health information for the employee acquired via an interactive health survey; health status data for the employee acquired via one or more health sensor systems; and functional performance test data for the employee, the functional performance test data acquired via a virtual performance test conducted using an augmented virtual reality (AVR) headset worn about the head of the employee and presenting, for viewing by the employee, a functional performance test including a virtual scene including one or more virtual objects for the employee to interact with, and the functional performance test data for the employee being indicative of the interactions of the employee with the one or more virtual objects; determining a resiliency score for the employee based at least in part on the set of resiliency data, the resiliency score indicating a change in a cost associated with the employee over a given period of time; determining that the employee is recommended for promotion to a leadership position within an organization based at least in part on the resiliency score; determining a ranking of the employee relative to other employees within the organization based at least in part on the resiliency score; and serving, to a first device for display to the employee, an employee leadership review dashboard including: an indication of the resiliency score for the employee; and an indication of the ranking of the employee relative to the other employees.

In certain embodiments, the program instructions are further executable by the one or more processors to cause: serving, to a second device for display to an employer, an employer leadership review dashboard including: an indication of the resiliency score for the employee; an indication that the employee is recommended for the promotion to the leadership position within the organization; and an indication of the ranking of the employee relative to the other employees.

In some embodiments, The medium of claim 17, the set of resiliency data is associated with a first time, and the program instructions are further executable by the one or more processors to cause: receiving a second set of resiliency data for the employee, the second resiliency data corresponding to health information for the employee at a second time, health status data for the employee at the second time, and functional performance test data for the employee at the second time, wherein the resiliency score is determined as a difference between a first value determined based on the set of resiliency data associated with the first time, and a second value determined based on the second set of resiliency data associated with the second time.

In certain embodiments, the program instructions are further executable by the one or more processors to cause: determining a score for the employee in a life area based at least in part on the set of resiliency data; determining whether the score for the employee in the life area satisfies a life area score threshold; and in response to determine that the score for the employee in the life area does not satisfy the life area score threshold, automatically scheduling one or more activities for the employee that are expected to improve the life area for the employee.

Provided in some embodiments is an employee management system including: an employee resiliency data acquisition system including: a virtual reality (VR) headset to be worn about the head of the employee and to present one or more virtual testing scenarios to the employee, the VR headset including a tracking device for tracking arm and hand movements of the employee while wearing the VR headset; a health sensor system to acquire health status data indicative of health conditions of the employee; and an employee leadership assessment system communicatively coupled to the employee resiliency data acquisition system via a communications network, the employee leadership assessment system including a non-transitory computer readable storage medium including program instructions stored thereon that are executable by one or more processors to cause: displaying, via the VR headset, a plurality of testing scenarios to the employee, wherein at least one of the testing scenarios includes a situation faced by the employee during a workday, and wherein at least one of the testing scenarios includes a functional performance test; obtaining, from the health sensor system, a set of resiliency data for the employee, the set of resiliency data including health status data indicative of performance of the employee in the plurality of testing scenarios displayed via the VR headset, and health conditions of the employee while engaged in the plurality of testing scenarios displayed via the VR headset; determining a resiliency score for the employee based at least in part on the set of resiliency data.

In certain embodiments, the program instructions are further executable to cause determining that the employee is recommended for a promotion to a leadership position within an organization based at least in part on the resiliency score; determining a ranking of the employee relative to other employees within the organization based at least in part on the resiliency score; serving, to a first device for display to the employee, an employee leadership review dashboard including: an indication of the resiliency score for the employee; and an indication of the ranking of the employee relative to the other employees; and serving, to a second device for display to an employer, an employer leadership review dashboard including: an indication of the resiliency score for the employee; an indication that the employee is recommended for the promotion to the leadership position within the organization; and an indication of the ranking of the employee relative to the other employees.

BRIEF DESCRIPTION OF THE DRAWINGS

FIGS. 8A and 8B illustrate display of first and second portions, respectively, of an example interactive health evaluation form graphical user interface (GUI) in accordance with one or more embodiments.

FIGS. 16A and 16B are charts that illustrate example physiological scores and performance test scores, respectively, for an employee in accordance with one or more embodiments.

FIG. 17 is an example lifestyle spider diagram that graphically illustrates scores for an employee's life areas in accordance with one or more embodiments.

Figure 1:
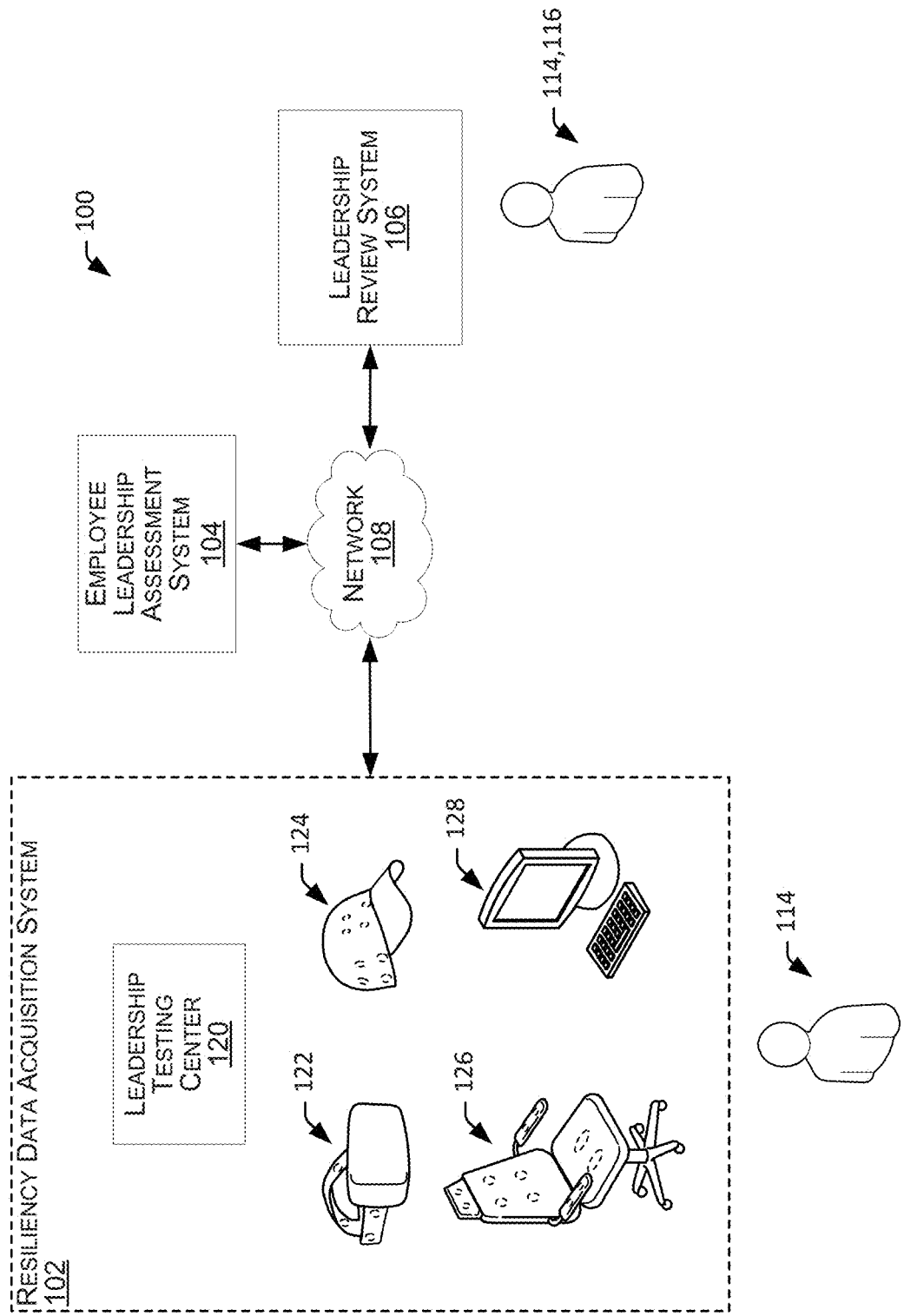
FIG. 1 is a block diagram that illustrates an example employee leadership development system in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

The present invention will now be described more fully hereinafter with reference to the accompanying drawings in which example embodiments of the invention are shown.

This invention may, however, be embodied in many different forms and should not be construed as limited to the illustrated embodiments set forth herein, rather, these example embodiments are provided so that this disclosure will be thorough and complete, and will fully convey the scope of the invention to those skilled in the art.

Described herein are systems and methods for acquiring and employing resiliency data for organizational leadership development programs. In some embodiments, resiliency data is acquired and used to identify, develop, and promote employees within an organization that exhibit leadership qualities, including a healthy lifestyle. In some embodiments, the resiliency data for an employee includes data that is indicative of the employee's health and lifestyle. For example, the resiliency data can include general health information (e.g., information about the employee's health risks, lifestyle, medical history, and/or the like), health status data (e.g., data indicative of the employee's current vital signs, such as blood pressure (BP) respiratory rate (RR), hear rate (HR), blood glucose level, brain activity, and/or the like), and functional performance data (e.g., data indicative of the employee's reaction skills, coordination skills, balance, flexibility, strength, endurance, and/or the like).

In some embodiments, the resiliency data can be used to generate employee leadership information that is indicative of the employee's potential to be a leader within the organization. For example, one or more algorithms can be applied to the resiliency data for an employee to generate one or more corresponding scores for the employee. As a further example, one or more lifestyle algorithms can be applied to the resiliency data for an employee to generate respective scores for various areas of the employee's life (e.g., physical environment, health and well-being, financial abundance, family and friends, career and job satisfaction, significant other, personal development and growth, and fun and recreation). As another example, a resiliency algorithm can be applied to the resiliency data for an employee to generate a resiliency score for the employee. In some embodiments, a resiliency score for an employee can be compared to resiliency scores for other employees to provide for comparisons of employees' leadership potential and development. For example, employees may be ranked based on resiliency scores, and employees with the highest resiliency scores may be automatically recommended or selected for leadership positions or other promotions.

In some embodiments, leadership information can be presented to employees and/or employers via interactive graphical user interfaces (GUIs), such as employee and/or employer dashboards. In some embodiments, an employee dashboard (also referred to herein as an "employee leadership dashboard") (e.g., similar to the dashboard 1000 described herein with regard to at least FIG. 10) can be accessible by a particular employee and can include leadership information for the employee, such as the employee's resiliency score, a ranking of the employee relative to other employees based on her/his resiliency score, a leaderboard that includes a listing of the current employee rankings, a lifestyle spider diagram and/or chart that indicates the employee's scores in various life areas, and/or links to challenges (or suggestions) for improving the various life areas and scores. For example, if an employee has a relatively low score (e.g., below her/his goal score) for the "friends and family" life area, the dashboard may include a corresponding "challenge" link that can be selected by the employee to navigate to content that can help the employee to improve that area of her/his life, and, thereby improve the score for that life area. In some embodiments, the content can include suggestions or instructions on how to improve the life area. For example, if the "challenge" link for the "friends and family" life area is selected, the employee may be presented with the following suggestion: "For the next month, set aside 1 evening during each work week and ½ day during each weekend that is reserved for interacting with your family." In some embodiments, activities to improve a life area or an employee can be automatically scheduled for the employee. For example, the employee's work calendar may be automatically populated with calendar entries/events for "Family Time," 1 evening during each of the work weeks and a ½ day during each of the weekends of the following month.

Figure 11A:
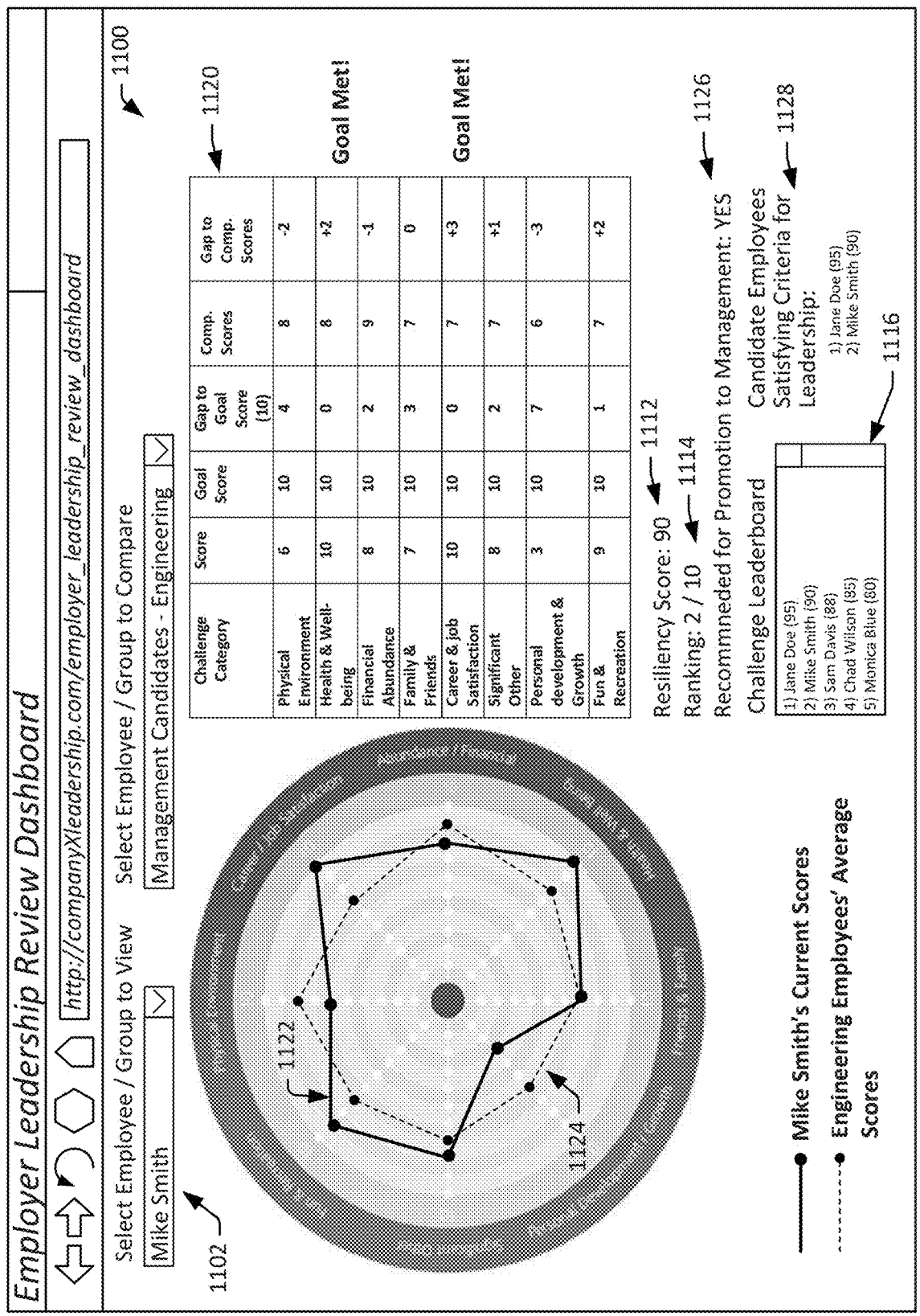
FIG. 11A is a diagram that illustrates an example employer (employee) leadership review dashboard in accordance with one or more embodiments.

In some embodiments, an employer-employee review dashboard (also referred to herein as an "employer leadership review dashboard") (e.g., similar to the dashboard 1100 described herein with regard to at least FIG. 11A) can be accessible by an employer (e.g., a manager or supervisor of one or more groups of employees) and can include leadership information for one or more employees or groups of employees. For example, the employer may be able to select whether she/he would like to view leadership information for a particular employee, a particular group of employees, and/or a view a comparison of the leadership information against one or more other employees or groups of employees. In some embodiments, the leadership information can include, for the selected employee or group of employees, a resiliency score, a ranking of the employee/group relative to other employees/groups based on resiliency scores, a leaderboard that includes a listing of the current employee rankings, a lifestyle spider diagram and/or chart that indicates the employee's/group's scores in various life areas, an indication of whether an employee is recommended for promotion to management, a listing of employees that are recommended for promotion to management, and/or the like. Such a dashboard may provide the employer with an efficient way to assess the progress of leadership development by employees and/or groups of employees.

Figure 11B:
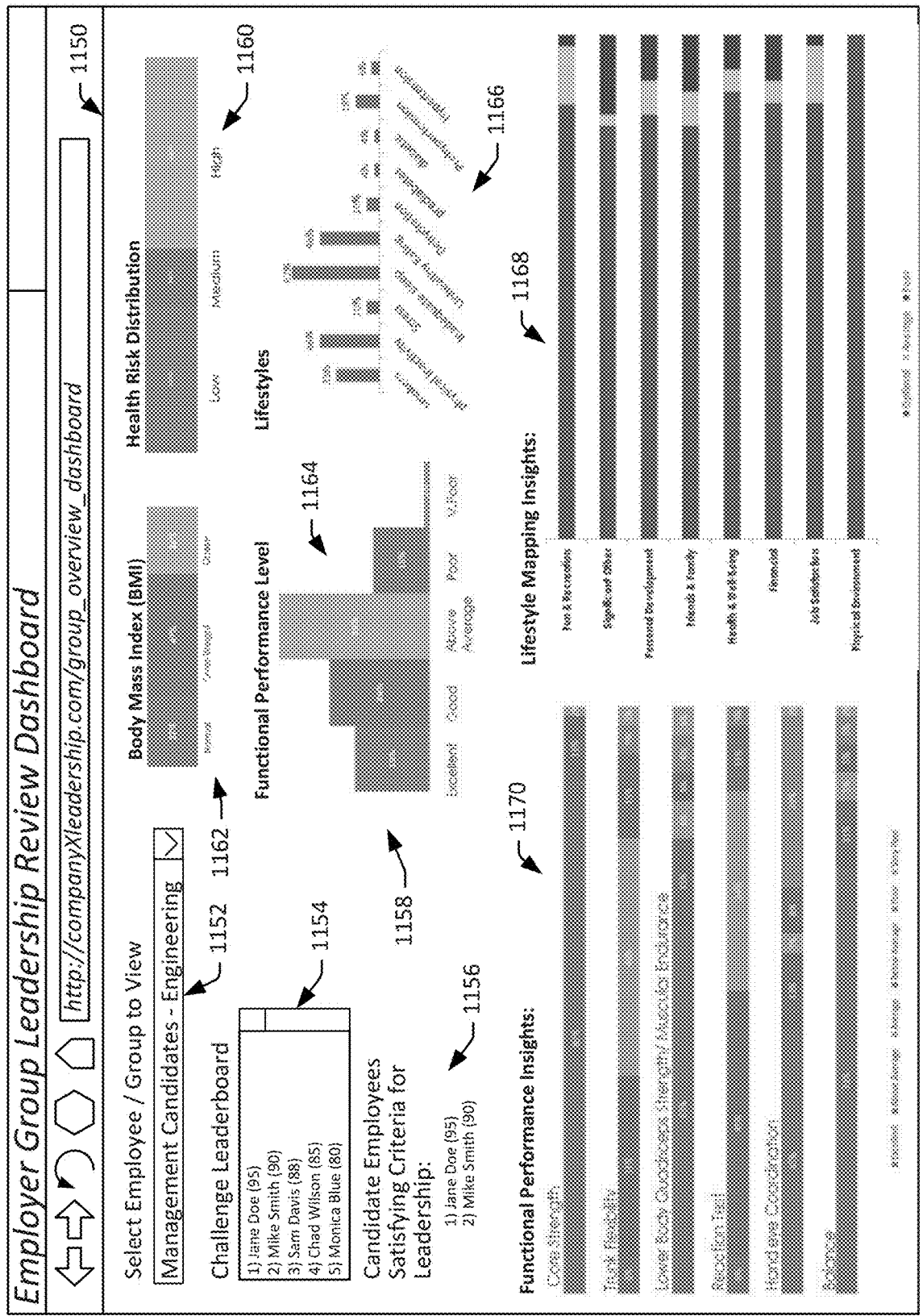
FIG. 11B is a diagram that illustrates an example employer (group) leadership review dashboard in accordance with one or more embodiments.

In some embodiments, an employer-group review dashboard (also referred to herein as an "employer group review dashboard") (e.g., similar to the dashboard 1150 described herein with regard to at least FIG. 11B) can be accessible by an employer (e.g., a manager or supervisor of one or more groups of employees) and can include leadership information for groups of employees. For example, the employer may be able to select whether she/he would like to view leadership information for a particular group of employees (e.g., an "engineering management candidates" group). In some embodiments, the leadership information can include a resiliency score for the group, a ranking of the employees in the group based on respective resiliency scores, a leaderboard that includes a listing of the current employee rankings, a listing of employees in the group that are recommended for promotion to management, and various informational charts for the group (e.g., charts regarding the group's distribution of health risks, body mass index, functional performance levels, lifestyles, lifestyle mapping insights, functional performance insights, and/or the like).

In some embodiments, resiliency data can be obtained via a resiliency data acquisition systems, such as via leadership testing centers (LTCs) (also referred to as "pop-up" clinics). In some embodiments, an LTC can include systems for the submission of general health information and/or systems for acquiring health status data, functional performance data, and/or the like. In some embodiments, an LTC can be used to acquire baseline resiliency data for candidate employees, and this baseline data can be supplemented with other "follow-up" resiliency data, such as updated resiliency data acquired during subsequent employee visits (e.g., weekly visits) to the leadership testing centers, or during the course of work (e.g., via real-time health monitoring system provided in the candidate employee's work environment).

In some embodiments, an LTC can include a terminal that displays an interactive health information GUI for use by an employee or a health care practitioner to submit general health information for the employee. For example, upon arriving at an LTC, an employee may visit a terminal to fill out an interactive health evaluation that includes questions regarding the employee's health risks, lifestyle, medical history, and/or the like. In some embodiments, an LTC can include one or more health status sensing systems for acquiring health status data for employees. For example, after completing the health evaluation, the employee may be subjected to one or more health status tests that employ various health sensors (e.g., in health-sensing chairs, health-sensing caps, health-sensing-VR headsets, and/or the like) to acquire the employee's current vital signs and other health metrics, such as blood pressure (BP) respiratory rate (RR), hear rate (HR), blood glucose level, and/or the like. In some embodiments, an LTC can include one or more functional performance sensing systems for acquiring functional performance data for employees. For example, after completing the one or more health status tests, the employee may be subjected to one or more functional performance tests to acquire data indicative of the employee's reaction skills, coordination skills, balance, flexibility, strength, endurance, and/or the like.

In some embodiments, the functional performance tests can include physical test, such as a reaction test (e.g., a drop test with scoring based how quickly the employee can catch a falling object), a coordination test (e.g., a catch test with scoring based how many objects the employee can catch in a given time period), a balance test (e.g., a one-leg test with scoring based on how long the employee is able to remain standing on the one leg), a foundational strength test (e.g., a plank test with scoring based on how long the employee is able to maintain a plank position), an endurance test (e.g., a squat test with scoring based on how long the employees is able to maintain a squatting position), a flexibility test (e.g., a sit and reach test with scoring based on how far the employee is able to reach), and/or the like. A reaction test can demonstrate or otherwise be indicative of an employee's functional ability to have strong (quick) internal reaction to unforeseen external forces and circumstances. A coordination test can demonstrate or otherwise be indicative of an employee's ability to coordinate various functions at one time and maintain focus and direction. A balance test can demonstrate or otherwise be indicative of an employee's ability to remain centered and committed to the cause despite external forces. A strength test can demonstrate or otherwise be indicative of an employee's ability to have strong foundations (to the core) despite any instability or turbulence to remain well positioned and in strong alignment. An endurance test can demonstrate or otherwise be indicative of an employee's ability to endure and to keep going despite the discomfort and uncertainty in the sense of never giving up. A flexibility test can demonstrate or otherwise be indicative of an employee's ability to remain stable, yet flexible, and extend the limits of stability within reason and when required.

In some embodiments, acquisition of health status data can be facilitated by one or more specialized testing devices such as a health-sensing chair having integrated health sensors for acquiring health data (also referred to as a "smart-chair" or "hot-seat"), a health-sensing cap having integrated health sensors for acquiring health data (also referred to as a "smart-cap" or "thinking cap"), a VR headset having integrated health sensors for acquiring health data (also referred to as a "health-sensing VR-headset") and/or the like. In some embodiments, a health-sensing chair can include body temperature sensors, blood pressure sensors, glucose sensors, hear rate sensors, respiratory sensors, electroencephalogram (EEG) sensors, and/or the like integrated therein. In some embodiments, a health-sensing cap can include EEG sensors, temperature sensors, and/or the like integrated therein. Thus, for example, an employee may simply sit in the health-sensing chair and/or wear the health-sensing cap during a visit to the LTC, and the LTC can quickly conduct automated heath status test using the integrated sensors of the health-sensing chair and/or the health-sensing cap to acquire health status data for the employee.

In some embodiments, the health-sensing VR-headset can be used to conduct virtual functional performance tests. For example, the health-sensing VR headset may include an augmented VR (AVR) headset that can be worn on the head of the employee, and that can sense health data for the employee and/or generate virtual scenes visible to the employee. The scenes can include various scenes that that provide virtual reaction tests (e.g., quickly catching a falling object), virtual coordination tests (catching multiple objects flight), and or the like. For example, the health-sensing AVR headset may overlay a scene in an employee's real world view of the surrounding environment, and the scene can include a virtual drop test scene that includes an overlay of a virtual object (e.g., a ruler) falling in the employee's field of view (FOV) that the employee can catch (virtually) as it descends (e.g., the employee can grasp the falling ruler in space as it descends in the virtual environment). As another example, the scene can include a virtual catch test scene that includes an overlay of multiple virtual objects (e.g., balls) traveling toward the employee in the employee's field of view (FOV) that the employee can catch (virtually) (e.g., the employee can grasp the flying balls in space as they fly toward the employee in the virtual environment).

Such virtual test can reduce the physical complexity of the LTC and increase its flexibility. For example, an LTC employing such virtual test can be provided in a relatively small space, without the need to provide the actual object or space for conducting the respective test. Further, the LTC may be portable, or at least relatively non-intrusive and easy to setup in a work environment. The use of virtual tests can also improve the flexibility of test configurations. For example, the virtual test can be easily modified without having to physical add or remove components (e.g., rulers or balls). Further, test can be easily customized for particular employees of groups of employees. For example, a suite of performance tests for an employee or a group of employees can include a drop test and/or catch test with objects of a given size moving at given rates of speed, and a suite of performance tests for another employee or another group of employees can include a drop test and/or catch test with objects of a different size moving at different rates of speed. Accordingly, the implementation of virtual tests can provide for a streamlined and highly-flexible LTC.

Figure 2:
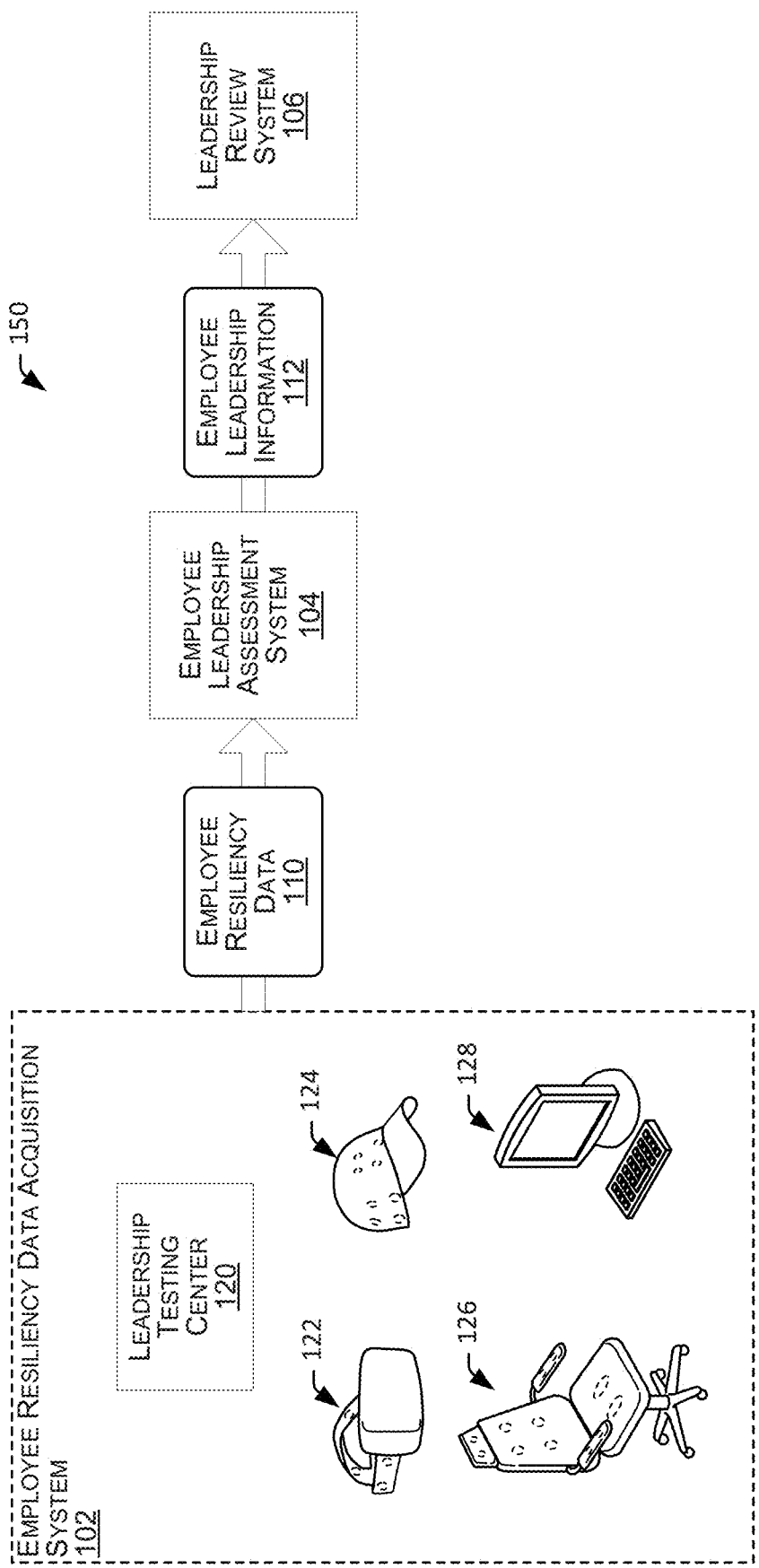
FIG. 2 is a block diagram that illustrates an example dataflow in an employee leadership development system in accordance with one or more embodiments.

FIG. 1 is a block diagram that illustrates an example employee leadership development (ELD) system 100 in accordance with one or more embodiments. In some embodiments, the ELD system 100 includes a resiliency data acquisition system 102, an employee leadership assessment system 104 and a leadership review system 106 communicatively coupled via a network 108. FIG. 2 is a block diagram that illustrates an example dataflow 150 in an ELD system 100 in accordance with one or more embodiments. In some embodiments, employee resiliency data 110 (e.g., acquired via the resiliency data acquisition system 102) is provided to the employee leadership assessment system 104, and the employee leadership assessment system 104 processes the resiliency data 110 to generate corresponding employee leadership information 112 that can be provided to one or more leadership review systems 106 for presentation to a user (e.g., an employee 114 and/or an employer 116) and/or the like.

The network 108 may include an element or system that facilitates communication between the entities of the system 100. For example, the network 108 may include an electronic communications network, such as the Internet, a local area network (LAN), a wide area network (WAN), a wireless local area network (WLAN), a cellular communications network, and/or the like. In some embodiments, the network 108 can include a single network or a combination of networks.

The resiliency data acquisition (RDA) system 102 may include one or more devices or sub-systems for acquiring resiliency data 130 (e.g., including general health information, health status data, functional performance data, and/or the like). For example, the RDA system 102 may include one or more leadership testing centers (LTC) 120, one or more health-sensing VR headsets 122, one or more health-sensing caps 124, one or more health-sensing chairs 126, one or more terminals 128, and/or the like. In some embodiments, an LTC 120 can include one or more health-sensing VR headsets 122, one or more health-sensing caps 124, one or more health-sensing chairs 126, and/or one or more terminals 128. Thus, for example, general health information, health status data, functional performance data, and/or the like from an employee 114 can be acquired in a single visit to the LTC 120. In some embodiments, one or more of a health-sensing VR headset 122, a health-sensing cap 124, a health-sensing chair 126, a terminal 128, and/or the like can be provided remote from (e.g., outside of) the LTC 120. For example, a health-sensing VR headset 122, a health-sensing cap 124, a health-sensing chair 126, a terminal 128, and/or the like can be provided in a workstation for an employee 114 such that the employee 114 general health information, health status data, functional performance data, and/or the like can be acquired while the employee is engaged in her/his work duties. In some embodiments, devices can be provided at one or both of an LTC 120 and locations remote from the LTC 120. For example, an employee 114 may visit an LTC 120 on a regular basis (e.g., weekly) and "baseline" LTC resiliency data 110 can be acquired during the visit, and "updated" resiliency data 110 can be acquired daily using remote systems located at her/his workstation. Such a system may provide increased convenience to the employee 114, as well as enabling the system 100 to provide updated employee leadership information 112 in real-time such that the employee 114 can remain aware of her/his status and engaged in the leadership health development program and/or the employer 116 can be made aware of the progress of the employee 114.

In some embodiments, a terminal 128 can include any variety of electronic devices that provide for the submission of general health information for an employee 114, such as one or more electronic computing devices. A terminal 128 may include, for example, a desktop computer, and/or one or more mobile computing devices, a laptop computer, a tablet computer, a personal digital assistant (PDA), a smartphone, a wearable computer device (e.g., a smart watch), a gaming console, and/or the like. In some embodiments, a terminal 128 can include a networked device capable of communicating information via the network 108. A terminal 128 may be a client of the employee leadership assessment system 104. In some embodiments, a terminal 128 can include various input/output (I/O) interfaces, such as a display screen (e.g., for displaying graphical user interfaces (GUIs)), an audible output interface (e.g., a speaker), an audible input interface (e.g., a microphone), an image acquisition interface (e.g., a camera), a biometric interface (e.g., an eye or fingerprint scanner), a keyboard, a pointer/selection device (e.g., a mouse, a trackball, a touchpad, a touchscreen, a stylus or the like), a printer, and/or the like.

In some embodiments, a terminal 128 can include general computing components and/or embedded systems optimized with specific components for performing specific tasks. A terminal 128 may include, for example, a leadership data acquisition application. The leadership data acquisition application may be, for example, a software application that is executed by the terminal 128 for acquiring general health information (e.g., information about the employee's health risks, lifestyle, medical history, and/or the like) from a user (e.g., a medical practitioner and/or an employee 114), and/or acquiring health status data (e.g., data indicative of the employee's current vital signs, such as blood pressure (BP) respiratory rate (RR), hear rate (HR), blood glucose level, and/or the like) and/or functional performance data (e.g., data indicative of the employee's reaction skills, coordination skills, balance, flexibility, strength, endurance, and/or the like) from one or more health-sensing VR headsets 122, one or more health-sensing caps 124, one or more health-sensing chairs 126, and/or the like. In some embodiments a terminal 128 can consolidate the received information, and transmit corresponding resiliency data 110 (e.g., including the acquired general health information, the health status data, and the functional performance data, or at least an indication thereof) to the employee leadership assessment system 104. In some embodiments, a terminal 128 can include one or more computer systems similar to that of the computer system 1000 described below with regard to at least FIG. 10.

In some embodiments, a health-sensing VR headset 122 can include a device for presentation of one or more virtual scenes to a user, such an employee 114 wearing the health-sensing VR headset 122. In some embodiments, the health-sensing VR headset 122 includes an augmented reality VR headset that overlays a virtual scene over a real-world view of a surrounding environment. Thus, for example, an employee 114 wearing the headset may be presented with a virtual scene (e.g., including elements of a functional health test) overlaid onto/over the normal field of view (FOV) of the employee 114, (e.g., overlaid onto a view of the environment located in front of the employee 114 and that that would be visible to the employee 114 if the employee were not wearing the health-sensing VR headset 122). In some embodiments, the health-sensing VR headset 122 can include additional sensors (e.g., EEG sensors) that can acquire health data (e.g., brain activity data) while an employee 114 is wearing the health-sensing VR headset 122 and interacting with the virtual scenes presented by the health-sensing VR headset 122.

Figure 3:
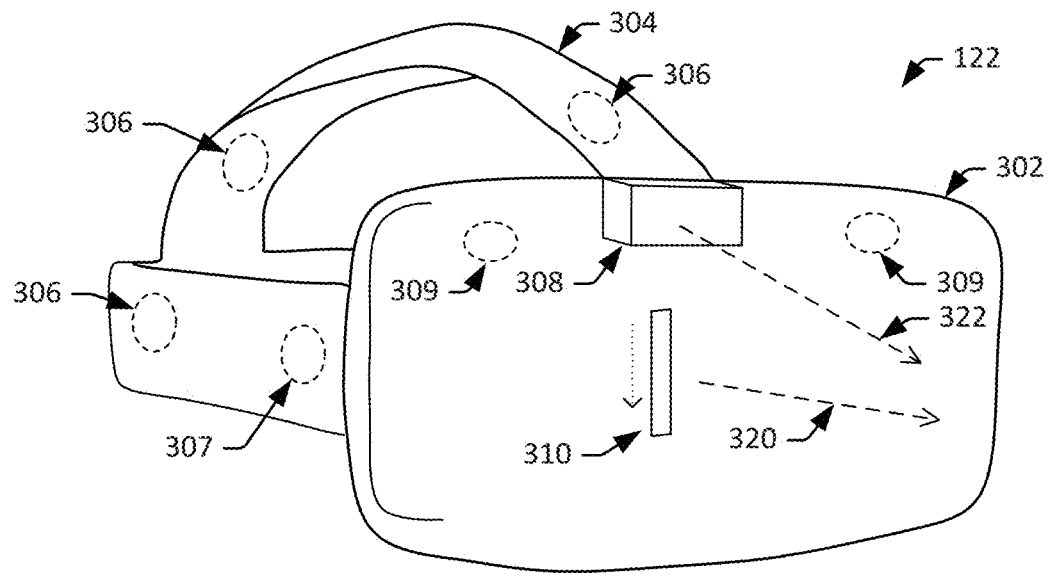
FIG. 3 is a diagram that illustrates an example health-sensing virtual reality headset system in accordance with one or more embodiments.

FIG. 3 is a diagram that illustrates an example health-sensing VR headset (VR headset) 122 in accordance with one or more embodiments. In some embodiments, the VR headset 122 can include a VR display screen 302 (e.g., visible by a user wearing the headset 122), a headband (or head mount) 304, one or more health sensors 306, one or more auditory devices 307, a tracking system 308, and/or one or more eye tracking devices 309. In some embodiments, the VR display screen 302 includes a transparent panel on which a virtual scene 310 (e.g., a ruler falling in the field of view of the employee 114 during a drop test) can be displayed for viewing by a person wearing the headset 122. In some embodiments, the health sensors 306 can include sensors for acquiring brain health status data for an employee 114, while the employee 114 is wearing the VR headset 122. For example, health sensors 306 may include one or more EEG sensors for sensing brain activity of an employee 114 while the employee 114 is engaged in a functional performance test, such as a drop test. The health sensors 306 can include sensors for acquiring health data that can be used for determining other characteristics, such as temperature sensors (e.g., that can be used to sense and determine body (or scalp) temperature), electro-dermal activity (EDA) sensors (e.g., galvanic skin response (GSR)) for sensing electrical characteristics of the skin (e.g., that can be used to sense and determine stress levels of the employee 114), and/or the like. In some embodiments, some or all of the health sensors 306 may transmit the health status data (e.g., indicative of brain activity) wirelessly (e.g., via Bluetooth communication) to another device, such as a terminal 128.

In some embodiments, a tracking system 308 can include a device for tracking the physical movements of an employee wearing the VR headset 122. For example, the tracking system 308 may include an infrared (IR) tracking system for determine the positions and/or movements of the hands of an employee 114 while the employee 114 is engaged in a functional performance test, such as a drop test. In some embodiments, the tracking system 308 is physically integrated with the VR headset 122. For example, the tracking system 308 may include an IR tracking system 308 having a tracking region (e.g., an IR "field of view" (IR-FOV)) that is aligned with the FOV of the VR headset 122, such that the IRFOV overlaps some or all of the FOV of the VR headset 122, and the tracking system 308 may include, for example, an IR tracking device that is fixed or otherwise coupled to the VR headset 122 such that its IRFOV remains aligned with the FOV of the VR headset 122. Thus, for example, when an employee 114 wearing the IR headset 122 is looking in a first direction (e.g., the employee 114 has her/his head positioned to look to her/his left) such that the VR headset 122 presents a corresponding first FOV to the employee 114 that is associated with the direction (e.g., a view looking to her/his left), the tracking system 308 is also pointed in the first direction (e.g., due to its physical integration with the VR headset 122) such that the IRFOV aligns with the first FOV. Movement by the employee 114 (e.g., hand movements to the left of the employee 114) in the IRFOV can be tracked, and corresponding movements may be replicated in the FOV of the VR headset 122 displayed to the employee 114 (e.g., displaying the employee 114 grasping at an object to her/his left based on corresponding movements in the IRFOV that are tracked by the tracking system 308). When the employee 114 wearing the IR headset 122 is looking in a second direction (e.g., the employee 114 has her/his head positioned to look to her/his right) such that the VR headset 122 presents a corresponding second FOV to the employee 114 that is associated with the direction (e.g., a view looking to her/his right), the tracking system 308 is also pointed in the second direction (e.g., due to its physical integration with the IR headset 122) such that the IRFOV aligns with the second FOV. Movement by the employee 114 (e.g., hand movements to the right of the employee 114) in the IRFOV can be tracked, and corresponding movements may be replicated in the FOV of the VR headset 122 displayed to the employee 114 (e.g., displaying the employee 114 grasping at an object to her/his right based on corresponding movements in the IRFOV that are tracked by the tracking system 308).

In some embodiments, the tracking system 308 may include an IR tracking device that is, for example, fixed at or near a top, right, left or bottom of a front portions of the VR headset 122. In some embodiments, an IR tracking device positioned at or near a top of the VR headset 122 may be directed in a slightly downward direction such that the IR FOV remains generally aligned with the FOV of the VR headset 122, and also includes the area in below the FOV of the VR headset 122. For example, as depicted in the illustrated embodiment, the VR headset 122 may provide a view that is aligned with a first direction (e.g., generally horizontal, as indicated by arrow 320), and the IR tracking device may be directed in a slightly downward in second direction (e.g., about 1-15 degrees below horizontal, as indicated by arrow 322) such that the IR FOV intersects and remains generally aligned with the FOV of the VR headset 122, and also includes at least some of the area below the FOV of the VR headset 122. In such an embodiment, the IR tracking device may be well suited for tracking hand movements, arm movements and the like that typically occur in the lower portion of the FOV of the VR headset 122 and the employee 114 (e.g., hand movements, arm movements and the like that typically occur in front of the torso, head and face of the employee 114). Thus, the IR FOV may include some or all of the regions where hand and arm movements by the employee 114 are likely to occur.

Movement by the employee 114 (e.g., hand movements to the right of the employee 114) in the IRFOV can be tracked, and corresponding movements may be replicated in the FOV of the VR headset 122 displayed to the employee 114 (e.g., displaying the employee 114 swatting at an object to her/his right). Thus, the IRFOV of the tracking system 308 may follow the FOV of the VR headset 122 to provide for sensing and tracking or otherwise determining movements by the employee 114 (e.g. hand gestures by the employee 114) in the FOV of the VR headset 122. Such an integrated tracking system 308 may enable the determination of movements of the employee 114 without the employee needing to wear gloves, sensors (e.g., sensors disposed on the arm and hands), or other devices to track the positions and movements of the hands of an employee 114, thereby further enhancing the simplicity and portability of an LTC 120 employing such a VR headset 122.

In some embodiments, the one or more auditory devices 307 can include a device for transmitting an auditory stimulus to an employee 114 wearing the VR headset 122. For example, the one or more auditory devices 307 may include a speaker to be positioned at or near the ear (e.g., integrated in the headband 304 near the position of the ear of the employee 114) that can produce sounds (e.g., audible instructions, prompts and/or the like) that can be heard by the employee 114 while wearing the VR headset 122. In some embodiments, the one or more auditory devices 307 can include a bone conduction speaker positioned at or near the ear (e.g., integrated in the headband 304 near the position of the ear of the employee 114). Such a bone conduction speaker may be positioned to be in contact with the skin of the employee 114, just in front of or behind the ear of the employee 114. For example, two auditory devices 307 may include bone conduction speakers respectively positioned near the front left and right of the headband 304 (as depicted), such that they are positioned just in front or behind the right and left ears, respectively, of the employee 114 when the VR headset 122 is worn by the employee 114.

In some embodiments, the one or more eye tracking devices 309 can include one or more devices for tracking eye characteristics and movements. For example, the one or more eye tracking devices 309 can include one or more cameras integrated into the VR headset 122 each having a FOV of one or both of the eyes of the employee 114, and being configured to capture video images of thereof. Such images may be processed to determine and track movement of the eyeball of the eye or eyes of the employee 114 (e.g., to determine an eye movement rate for the employee 114 when engaged in various VR activities), determine and track blinking of by the employee 114 (e.g., to determine a blink rate for the employee 114 when engaged in various VR activities), determine and track pupil size (e.g., to determine pupil dilatation/construction for the employee 114 when engaged in various VR activities). In some embodiments, such information can be used to present a "mirrored" avatar to the employee 114. For example, the employee 114 may be presented with a TPS (third person shooter) avatar with eye characteristics and movements (e.g., in real-time) that correspond to those of the employee 114 (e.g., including eye movements, pupil dilation and blinking that corresponds to those of the employee 114). This may provide a real-time reflection of self to the employee 114 in the VR environment, including, for example, testing scenarios. Such a sensory-immersive environment may be important in testing and training scenarios as it can help the employee 114 to recall core lessons and experiences more effectively through emotional memory.

Figure 4:
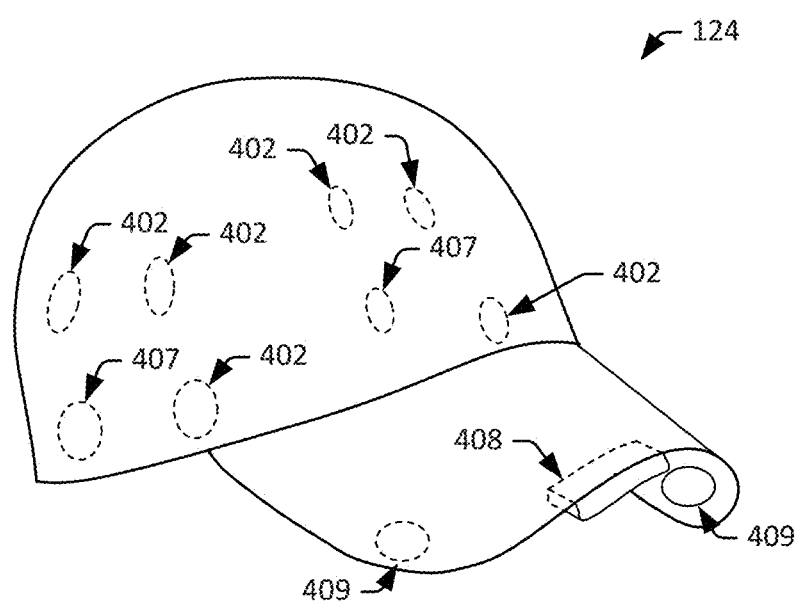
FIG. 4 is a diagram that illustrates an example health-sensing cap in accordance with one or more embodiments.

In some embodiments, a health-sensing cap ("cap") 124 can include a device to be worn on the head of a person. For example, a cap 124 may be worn on the head of an employee 114 while visiting an LTC 120 and/or throughout her/his work day (e.g. when the employee is engaged in her/his work duties). In some embodiments, the cap 124 can be used in scenarios similar to those described herein with regard to the VR headset 122. For example, employees 114 that not comfortable wearing the VR headset 122 (e.g., employees 114 susceptible to claustrophobia or motion sickness, and/or the like) may choose to wear the cap 124 during testing scenarios. FIG. 4 is a diagram that illustrates an example cap 124 in accordance with one or more embodiments. In some embodiments, the cap 124 can include sensors and devices similar to those provided in the VR headset 122. For example, the cap 124 may include a one or more health sensors 402 (e.g., similar to health sensors 306), one or more auditory devices 407 (e.g., similar to auditory devices 307 for positioning near the ear), a tracking system 408 (e.g., similar to tracking system 407 and fixed, for example, the bill of the cap 124), and/or one or more eye tracking devices 409 (e.g., similar to eye tracking devices 309 and provided under the bill of the cap 124). In some embodiments, the cap 124 can include one or more health sensor 402 disposed about an interior of the cap 124 such that the sensors 402 contact at least a portion of the scalp of the employee 114 while the employee 114 is wearing the cap 124. The health sensors 402 can include sensors for acquiring brain health status data for an employee 114, while the employee 114 is wearing the cap 124. For example, health sensors 402 may include EEG sensors for sensing brain activity of an employee 114 while the employee 114 is engaged in a functional performance test, such as a drop test, while the employee 114 is visiting the LTC 120, and/or while the employee 114 is engaged in normal work duties (e.g., working in an oil field, working at her/his workstation, and/or the like). The health sensors 402 can include sensors for acquiring health data that can be used for determining other characteristics, such as temperature sensors (e.g., that can be used to sense and determine body (or scalp) temperature), electrodermal activity (EDA) sensors (e.g., galvanic skin response (GSR)) for sensing electrical characteristics of the skin (e.g., that can be used to sense and determine stress levels of the employee 114), and/or the like.

In some embodiments, the one or more auditory devices 307 can include a bone conduction speaker to be positioned at or near the ear (e.g., integrated in the headband of the cap 124, near the position of the ear of the employee 114). Such a bone conduction speaker may be positioned to be in contact with the skin of the employee 114, just in front of or behind the ear of the employee 114. For example, two auditory devices 307 may include bone conduction speakers respectively positioned near the front left and right of the headband of the cap 124 (as depicted) such that they are positioned just in front of or behind the right and left ears, respectively, of the employee 114 when the cap 124 is worn by the employee 114.

In some embodiments, the cap 124 may be worn by the employee 114 while viewing video screen that provides a visual experience and scenarios that are the same or similar to those provided via the VR headset 122. For example, the employee 114 may be presented with a video screen displaying an avatar mimicking her/his movements in a virtual testing environment displayed on the video screen. Although certain embodiments include a traditional "baseball" cap, embodiments can include any suitable for of headwear, such as a headband, a stocking cap, a safety helmet, and/or the like. In some embodiments, some or all of the health sensors 402 may transmit the health status data (e.g., indicative of brain activity) wirelessly (e.g., via Bluetooth communication) to another device, such as a terminal 128.

Figure 5:
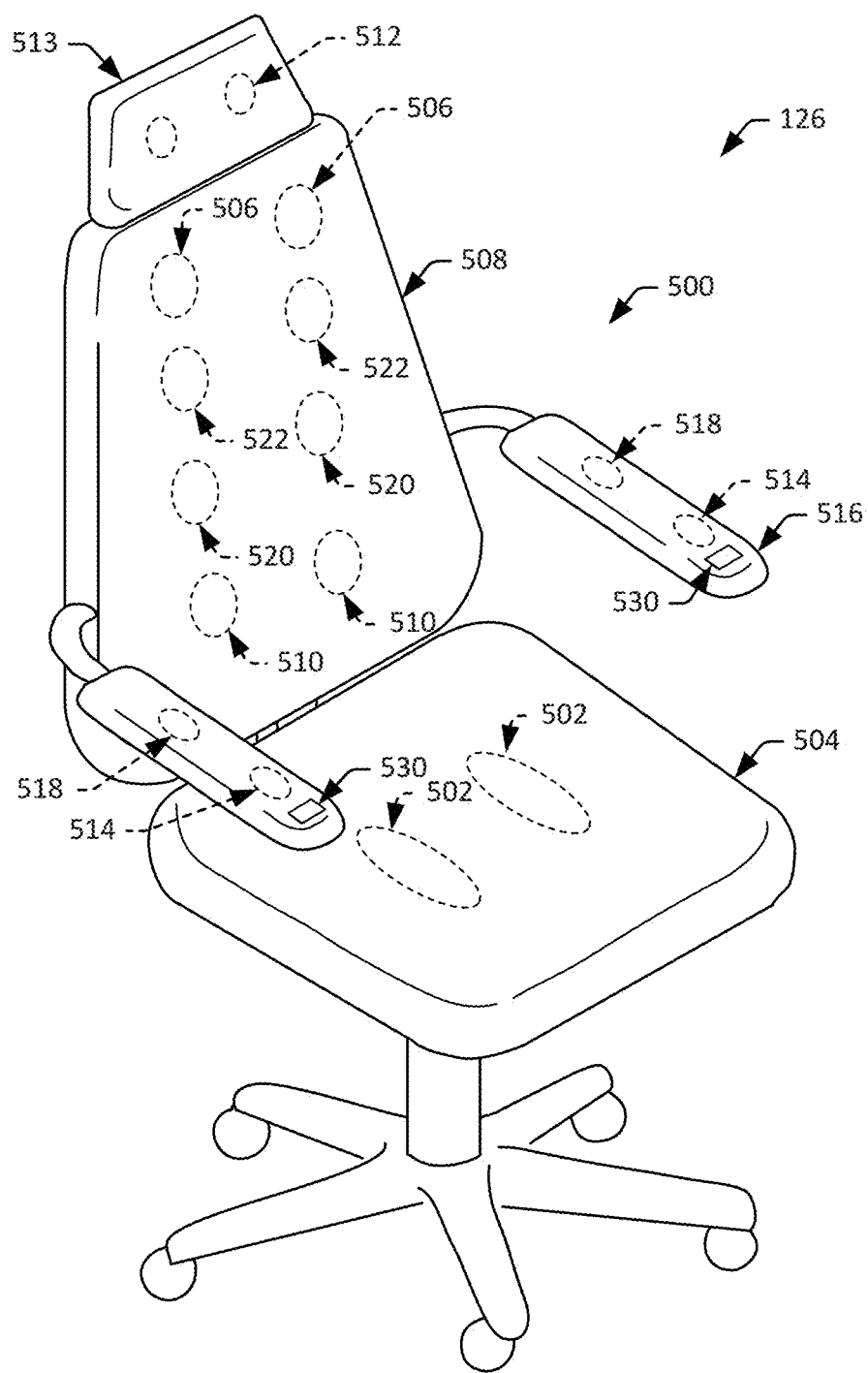
FIG. 5 is a diagram that illustrates an example health-sensing chair in accordance with one or more embodiments.

In some embodiments, a health-sensing chair ("chair") 126 can include a device in which an employee 114 can be seated. For example, a chair 124 may be located in an LTC 120, and an employee 114 may sit in the chair 124 while visiting the LTC 120. As a further example, a chair 124 may be located in a workstation for an employee 114, and she/he may sit in the chair 124 while engaged in her/his work duties at the workstation. In some embodiments, and employee 114 may wear a VR headset 122 and a cap 124 while seated in the chair 126. This may provide for sensing a variety of health characteristics of the employee 114, such as those discussed with regard to the VR headset 122, the cap 124 and the chair 126. FIG. 5 is a diagram that illustrates an example chair 126 in accordance with one or more embodiments. In some embodiments, the chair 124 can include one or more health sensors 500. The health sensors 500 can include various sensors for acquiring health status data for an employee 114 while the employee 114 is seated in the chair 126. For example, health sensors 500 may include one or more body temperature sensors 502 disposed in or on a bottom-seat portion 504 of the chair 126 for sensing a body temperature of the employee 114 while she/he is seated in the chair 126, one or more heart rate sensors 506 disposed in or on an upper-back portion 508 of the chair 126 for sensing a heart rate of the employee 114 while she/he is seated in the chair 126, one or more respiratory rate sensors 510 disposed in or on the upper-back portion 508 of the chair 126 for sensing a respiratory rate of the employee 114 while she/he is seated in the chair 126, one or more EEG sensors 512 disposed in or on a headrest 513 of the chair 126 for sensing a brain activity of the employee 114 while she/he is seated in the chair 126, one or more glucose sensors 514 disposed in or on armrests 516 of the chair 126 for sensing a blood glucose level of the employee 114 while she/he is seated in the chair 126, one or more blood pressure sensors 518 (e.g., a blood pressure cuff) disposed in or on the armrests 516 of the chair 126 for sensing a blood pressure of the employee 114 while she/he is seated in the chair 126, one or more EMG muscle tension sensors 520 disposed in or on the upper-back portion 508 of the chair 126 for sensing muscle tension of the employee 114 while she/he is seated in the chair 126, one or more position sensors 522 (e.g., a pressure sensor or an accelerometer) disposed in or on the upper-back portion 508 of the chair 126 for sensing body position and/or movement of the employee 114 while she/he is seated in the chair 126, and/or the like.

In some embodiments, a tracking system 530 can be provided to track movements of the employee 114 while seated in the chair 126. For example, a standalone IR tracking system (e.g., similar to tracking system 308) may be provided as a stand-alone system located proximate (e.g., in-front of) the chair 126 and having an IRFOV of a sitting region that includes the chair 126 and/or the employee 114 seated in the chair 126. The IR tracking system may track hand, arm and other body movements by the employee 114 while seated in the chair 126. In some embodiments, a tracking system can be integrated into the chair 126. For example, IR tracking systems 530 (e.g., similar to IR tracking devices 308) may be integrated into one or more of the armrest 516 of the chair 126, and have an IRFOV directed upward toward the hands, arms, torso, head and/or the like of the employee 114 to track hand movements, arm movements, torso movements, head movements and/or the like of the employee 114 while seated in the chair 126. In some embodiments, such information can be used to present a "mirrored" avatar to the employee 114. For example, the employee 114 may be presented with a TPS (third person shooter) avatar with movements (e.g., in real-time) that correspond to those of the employee 114. In some embodiments, some or all of the health sensors 502 may transmit corresponding health status data (e.g., indicative of body temperature, heart rate, respiratory rate, brain activity, glucose level, blood pressure, movement and/or the like for the employee 114) wirelessly (e.g., via Bluetooth communication) to another device, such as a terminal 128.

The employee leadership assessment (ELA) system 104 may include one or more devices for processing resiliency data 130 (e.g., including general health information, health status data, functional performance data, and/or the like) to generate corresponding employee leadership information 112. For example, the ELA system 104 may include a network server (or similar electronic computing device) that is configured to receive employee resiliency data 110 from the RDA system 102, process the resiliency data 110 to generate corresponding employee leadership information 112 (e.g., including employee and/or employer dashboards) and serve the employee leadership information 112 to one or more leadership review systems for presentation to one or more employees 114 and/or one or more employers 116. In some embodiments, the ELA system 104 can receive some or all of the resiliency data 130 directly from one or more devices of the employee resiliency data acquisition system 102. For example, a terminal 128 of an LTC 120 may consolidate separate portions of resiliency data 110 (e.g., including general health information submitted via the terminal 128, and health status data and/or functional performance data received from a VR headset 122, a cap 124, and/or a chair located at the LTC 126), and transmit the consolidated resiliency data 110 to a server of the ELA system 104. In some embodiments, other devices, such as a cap 124 and/or a chair located remote from the LTC 126 may transmit the resiliency data 110 to a server of the ELA system 104 via the network 108. In some embodiments, the ELA system 104 can include one or more computer systems similar to that of the computer system 1000 described below with regard to at least FIG. 10.

As described in more detail herein, in some embodiments, the ELA system 104 can process the resiliency data 130 for an employee 114 to generate employee leadership information 112 that is indicative of the employee's potential to be a leader within the organization. For example, the ELA system 104 may apply one or more algorithms to the resiliency data 130 for an employee 114 to generate one or more corresponding scores for the employee 114. For example, the ELA system 104 may apply one or more lifestyle algorithms to the resiliency data 110 for an employee 114 to generate respective scores for various life areas (e.g., physical environment, health and well-being, financial abundance, family and friends, career and job satisfaction, significant other, personal development and growth, and fun and recreation) of the employee 114. As a further example, the ELA system 104 may apply a resiliency algorithm to the resiliency data 110 for the employee 114 to generate a resiliency score for the employee 114. In some embodiments, the resiliency score for the employee 114 can be compared to resiliency scores for other employees 114 to provide for comparisons of leadership potential and/or development of the employees 114. For example, the ELA system 104 may rank employees 114 based on resiliency scores, and/or automatically recommend or select employees 114 with the highest resiliency scores for leadership positions or other promotions.

The leadership review system 106 may include one or more devices for presenting employee leadership information 112 to employees 114 and/or employers 116, such as one or more electronic computing devices. The leadership review system 106 may include, for example, a desktop computer, and/or one or more mobile computing devices, such as a laptop computer, a tablet computer, a personal digital assistant (PDA), a smartphone, a wearable computer device (e.g., a smart watch), a gaming console, and/or the like. In some embodiments, a leadership review system 106 can include a networked device capable of communicating information via the network 108. A leadership review system 106 may be a client of the employee leadership assessment system 104. In some embodiments, a leadership review system 106 can include various input/output (I/O) interfaces, such as a display screen (e.g., for displaying graphical user interfaces (GUIs)), an audible output interface (e.g., a speaker), an audible input interface (e.g., a microphone), an image acquisition interface (e.g., a camera), a biometric interface (e.g., an eye or fingerprint scanner), a keyboard, a pointer/selection device (e.g., a mouse, a trackball, a touchpad, a touchscreen, a stylus or the like), a printer, and/or the like.

In some embodiments, a leadership review system 106 can include general computing components and/or embedded systems optimized with specific components for performing specific tasks. A leadership review system 106 may include, for example, a leadership data review application. The leadership data review application may be, for example, a software application that is executed by the leadership review system 106 for presenting employee leadership information 112 to employees 114 and/or employers 116. For example, the leadership data review application may provide for the display of employee dashboards and/or employer dashboards, as described in more detail herein with regard to at least FIGS. 10, 11A and 11B. In some embodiments, a leadership review system 106 can include one or more computer systems similar to that of the computer system 1000 described below with regard to at least FIG. 10.

Figure 6:
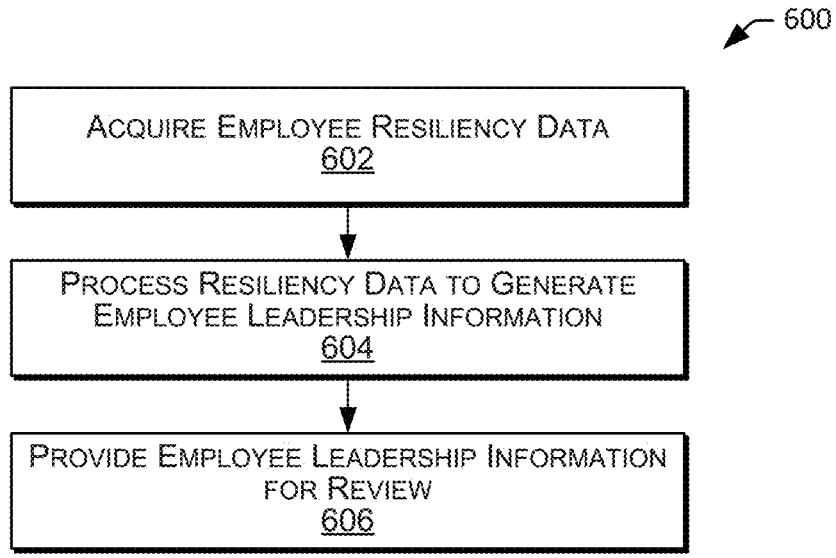
FIG. 6 is a flowchart that illustrates an example method of providing employee leadership information in accordance with one or more embodiments.

FIG. 6 is a flowchart that illustrates an example method 600 of providing employee leadership information in accordance with one or more embodiments. In some embodiments, the method 600 can generally include acquiring employee resiliency data (block 602), processing the employee resiliency data to generate employee leadership information (block 604), and providing employee leadership information for review (block 606). In some embodiments, some or all of the operations of method 600 may be performed by one or more components of the system 100.

In some embodiments, acquiring employee resiliency data (block 602) can include the RDA system 102 acquiring resiliency data 110 for one or more employees 114. For example, an employee 114 that is a candidate for a management position (e.g., a candidate employee 114) may visit a leadership testing center (LTC) 120, and resiliency data 110 for the employee can be acquired using one or more data acquisitions devices of the LTC 120, such as a VR headset 122, a cap 124, a chair 126, a terminal 128, and/or the like, as described herein. The resiliency data 110 may include general health information (e.g., information about the employee's health risks, lifestyle, medical history, brain activity, and/or the like), health status data (e.g., data indicative of the employee's current vital signs, such as blood pressure (BP) respiratory rate (RR), hear rate (HR), blood glucose level, and/or the like), and functional performance data (e.g., data indicative of the employee's reaction skills, coordination skills, balance, flexibility, strength, endurance, and/or the like). In some embodiments, the resiliency data 110 can be provided to the employee leadership assessment system 104 by the resiliency data acquisition system 102.

Figure 7:
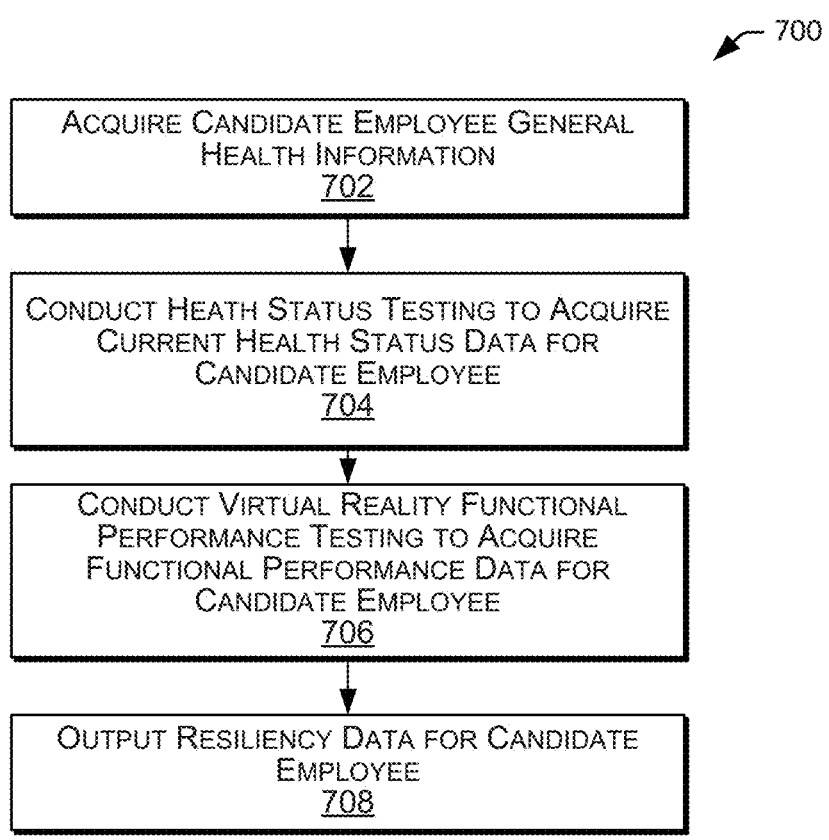
FIG. 7 is a flowchart that illustrates an example method of acquiring employee resiliency data in accordance with one or more embodiments.

FIG. 7 is a flowchart that illustrates an example method 700 of acquiring employee resiliency data in accordance with one or more embodiments. In some embodiments, the method 700 can generally include acquiring candidate employee general health information (block 702), conducting heath status testing to acquire current health status data for the candidate employee (block 704), conducting virtual reality (VR) based functional performance testing to acquire functional performance data for the candidate employee (block 706), and outputting corresponding resiliency data for the candidate employee (block 708). In some embodiments, some or all of the operations of method 700 can be performed by the resiliency data acquisition system 102.

Figure 8A:
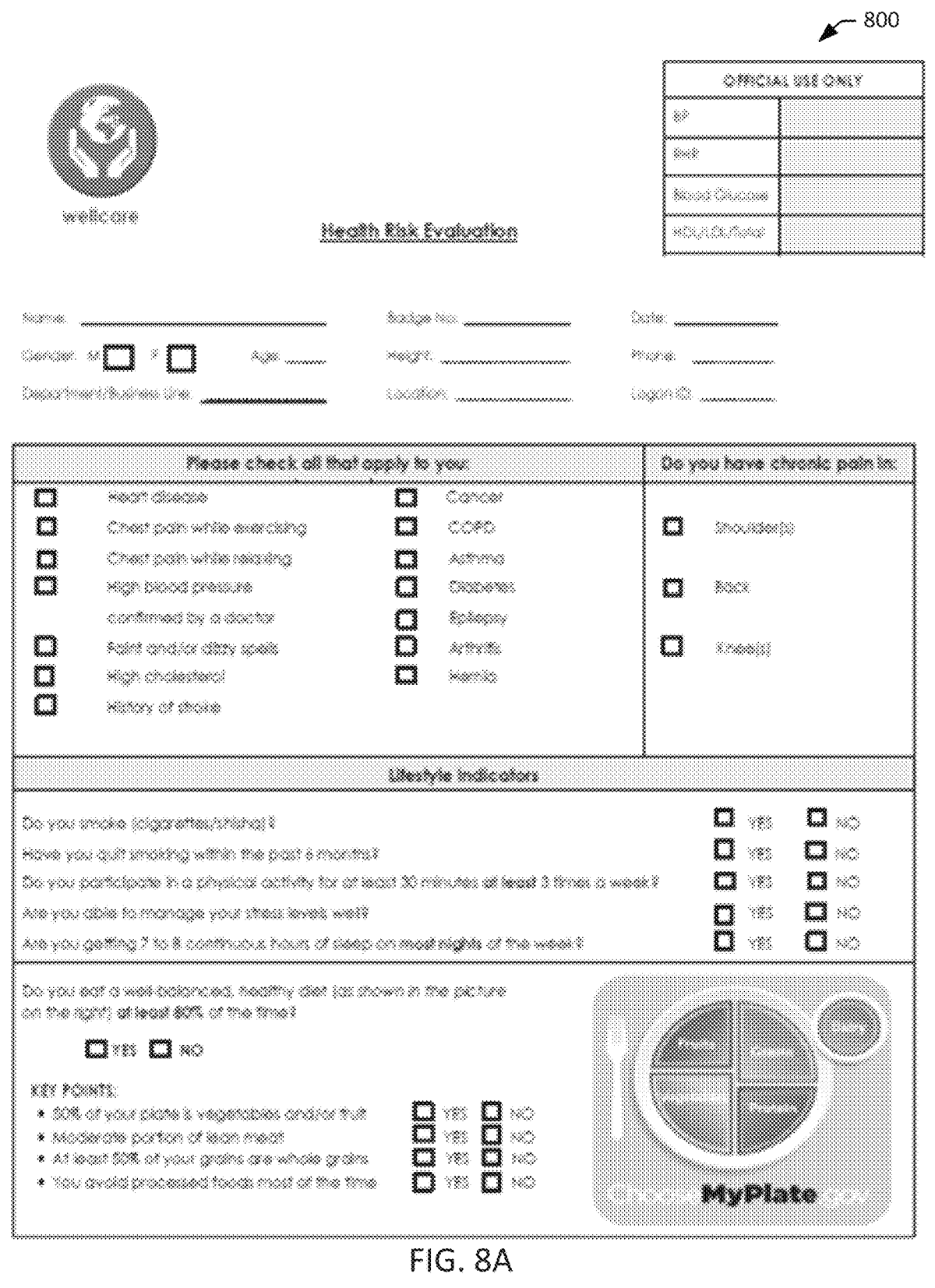
Figure 8B:
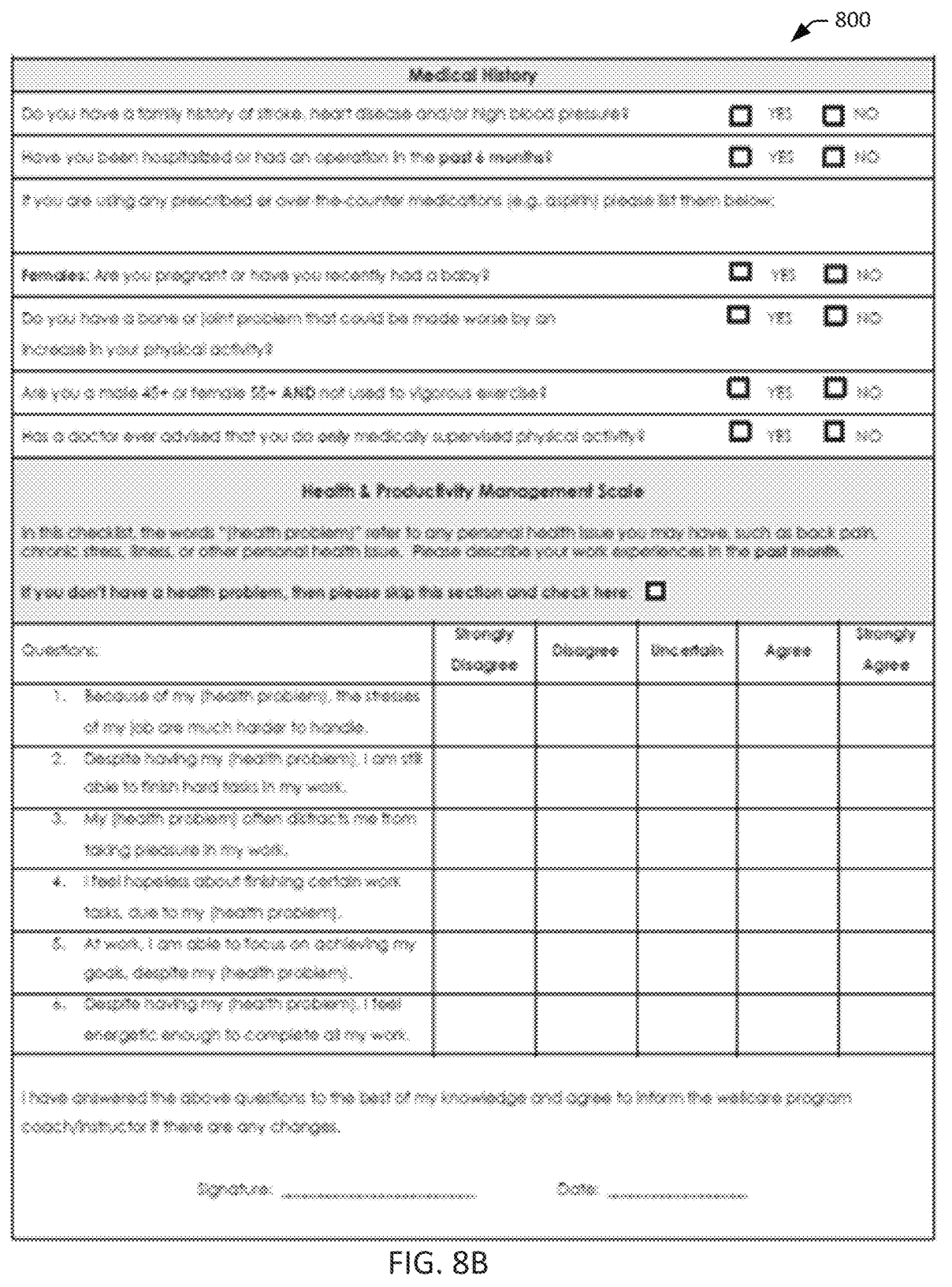

In some embodiments, acquiring candidate employee general health information (block 702) can include acquiring general health information for an employee via an interactive health evaluation form GUI presented to an employee at a terminal 128 of the resiliency data acquisition system 102. The evaluation can include, for example, questions regarding health risks, lifestyle, medical history, and/or the like for the employee 114. FIGS. 8A and 8B illustrate display of first and second portions, respectively, of an example interactive health evaluation form GUI 800 in accordance with one or more embodiments.

In some embodiments, conducting heath status testing to acquire current health status data for the candidate employee (block 704) can include conducting one or more automated test using various health sensors to acquire health status data indicative of current vital signs of the candidate employee 114. For example, the candidate employee 114 may sit in a chair 126 and/or wear a cap 124 while an automated suite of tests is run using the various health sensors 500 of the chair 126, the various health sensors 402 of the cap 124 and/or the various health sensors 306 of the VR headset 122 to acquire the blood pressure (BP) respiratory rate (RR), hear rate (HR), blood glucose level, brain activity, and/or the like for the employee 114.

In some embodiments, conducting virtual reality (VR) functional performance testing to acquire functional performance data for the candidate employee (block 706) can include conducting one or more functional performance tests to acquire functional performance data indicative of functional performance (e.g., reaction skills, coordination skills, balance, flexibility, strength, endurance, and/or the like) of the candidate employee 114. For example, the candidate employee 114 may take part in a reaction test (e.g., a drop test with scoring based how quickly the employee can catch a falling object), a coordination test (e.g., a catch test with scoring based how many objects the employee can catch in a given time period), a balance test (e.g., a one-leg test with scoring based on how long the employee is able to remain standing on the one leg), a foundational strength test (e.g., a plank test with scoring based on how long the employee is able to maintain a plank position), an endurance test (e.g., a squat test with scoring based on how long the employees is able to maintain a squatting position), a flexibility test (e.g., a sit and reach test with scoring based on how far the employee is able to reach), and/or the like. The functional performance data may include the results and/or scores for each of the functional performance tests conducted.

Figure 9A:
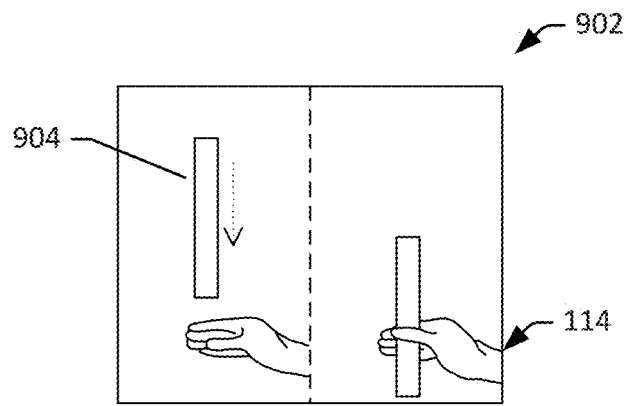
FIGS. 9A-9F are illustrations demonstrating various functional performance tests in accordance with one or more embodiments.
Figure 9B:
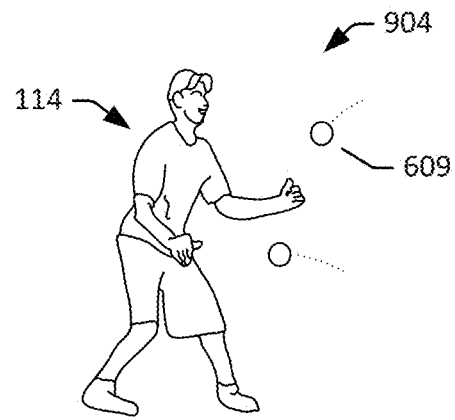
Figure 9C:
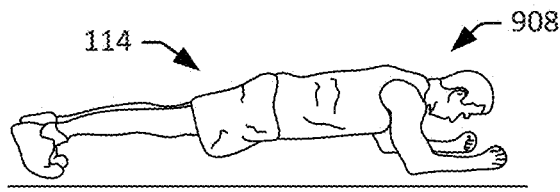
Figure 9D:
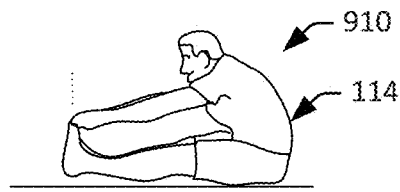
Figure 9E:
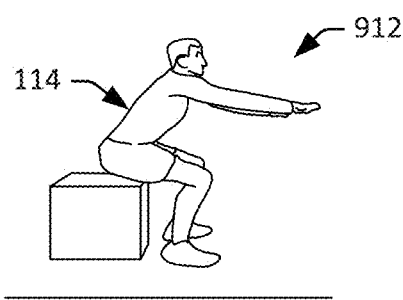
Figure 9F:
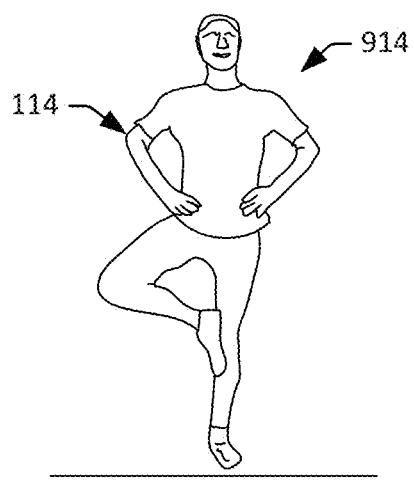

FIG. 9A-F are illustrations that demonstrate various example functional performance tests in accordance with one or more embodiments. FIG. 9A illustrates an employee 114 taking part in an example reaction test 902 in which an object 904 (e.g., a ruler) is dropped in front of the employee 114, and the employee 114 is tasked with catching the falling object 904 as quickly as she/he can. As described herein, in some embodiments, such a reaction test can be conducted using a virtual scene including a virtual object 904 that is visible to the employee 114 (e.g., in a FOV seen through a VR headset 122). FIG. 9B illustrates an employee 114 taking part in an example coordination test 904 in which one or more objects 906 (e.g., balls) are moving toward the employee 114, and the employee 114 is tasked with catching or hitting as many of the objects 906 as she/he can. As described herein, in some embodiments, such a coordination test can be conducted using a virtual scene including virtual objects 906 that is visible to the employee 114 (e.g., in a FOV seen through a VR headset 122). FIG. 9C illustrates an employee 114 taking part in an example foundational strength test 908 in which the employee 114 is tasked with reaming in a plank position (depicted) as long as she/he can. FIG. 9D illustrates an employee 114 taking part in an example a flexibility test 910 in which the employee 114 is tasked with attempting to reach as far has she/he can while seated (depicted). FIG. 9E illustrates an employee 114 taking part in an example endurance test 912 in which the employee 114 is tasked with maintaining a squatting position (as depicted) for as long as she/he can. FIG. 9E illustrates an employee 114 taking part in an example balance test 914 in which the employee 114 is tasked with maintaining a stance on one-foot (as depicted) for as long as she/he can.

In some embodiments, one or more of the functional performance tests can be completed (or supplemented) using virtual scenes provided via a virtual headset 122 worn by the employee 114 during the tests. For example, a reaction test can include an employee 114 viewing a virtual scene comprising a virtual object (e.g., a ruler) appearing to fall in the field of view (FOV) of the employee 114. The employee 114 may be tasked with grasping the virtual object as quickly as she/he can as the virtual object appears to fall within the FOV of the employee 114. When the employee 114 senses that the virtual object is falling, she/he may move her/his hand(s) into a position to physically grasp the virtual object as it appears to fall. Although the object is virtual (e.g., the object is just overlaid into the FOV, but is not physically present) such that the employee cannot physically catch the falling virtual object, her/his movement can be tracked (e.g., by a tracking system 308 of the VR headset 122) and the movements can be used to determine if, when and where the employee 114 "caught" the virtual object. As described herein, a score for the drop test can be determined based on how quickly the employee 114 was able to catch the falling object (e.g., with higher scores being assigned for quicker catches). Thus, such a reaction test can be performed without the use of an actual/physical falling object. Moreover, given the virtual nature of the reaction test, it can be accurately repeated for any number of employees, thereby eliminating variances across different tests, providing fair and consistent reaction test for all employees 114. Moreover, the test can be easily customized. For example, the reaction test can be made more difficult by reducing the size of the virtual object for an employee or a group of employees, and/or increasing the speed of the virtual object for another employee or another group of employees.

As a further example, a coordination test can include an employee 114 viewing a virtual scene comprising multiple objects (e.g., balls) appearing to move toward the employee 114 in the field of view (FOV) of the employee 114. Thus, the virtual objects may appear to be thrown toward or otherwise flying toward the employee 114. The employee 114 may be tasked with catching or hitting as many of the virtual objects as she/he can within a given time period. When the employee 114 senses that a virtual object moving toward her/him is close to her/him, she/he may move her/his hand(s) into a position to physically catch or hit the virtual object. Although the object is virtual (e.g., the object is just overlaid into the FOV, but is not physically present) such that the employee 114 cannot physically catch the virtual object, her/his movement can be tracked (e.g., by a tracking system 308 of the VR headset 122) and the movements can be used to determine if, when and where the employee 114 engaged (e.g., caught or hit) the virtual object. As described herein, a score for the coordination test can be determined based on how many of the virtual objects the employee 114 was able to engage (e.g., catch or hit) (e.g., with higher scores being assigned for more engagements). Thus, such a coordination test can be performed without the use of actual/physical flying objects. Moreover, given the virtual nature of the coordination test, it can be accurately repeated for any number of employees, thereby eliminating variances across different tests, providing fair and consistent reaction test for all employees 114. Moreover, the test can be easily customized. For example, the coordination test can be made more difficult by reducing the size of the virtual objects for an employee or a group of employees and/or increasing the speed and/or number of the virtual objects for another employee or another group of employees.

In some embodiments, a VR functional performance can be selected or customized based on the employee 114 taking part in the test. For example, if a first virtual catch test (e.g., including 5 balls simultaneously being moved toward the employee 114 at a rate of speed of 5 meter per second (m/s)) is associated with a first group of employees 114 in a first leadership development program, a second virtual catch test (e.g., including 10 balls simultaneously being moved toward the employee 114 at a rate of speed of 6 meter per second (m/s)) is associated with a second group of employees 114 in a second leadership development program, and the terminal 128 determines that the employee 114 being tested at the LTC 120 is in the first group of employees 114 based on her/his responses to the evaluation, then the terminal 128 may instruct the VR headset 122 to generate a VR functional performance test consistent with the first virtual catch test, and the VR headset 122 may generate a VR functional performance test including virtual scenes consistent with the first virtual catch test. Thus, the VR functional test can be automatically configured to correspond to the employee 114 being tested.

In some embodiments, conducting heath status testing to acquire current health status data for the candidate employee can include conducting suite of interactive test or challenges. Such interactive tests or challenges can, for example, be provided in a gaming environment. For example, the employee 14 may engage in a game (e.g., interactive tests or challenges) that includes complete multiple "chapters" of an employee's typical work day. During participation in the games various health sensors to acquire health status data indicative of current vital signs of the candidate employee 114. For example, the candidate employee 114 may sit in a chair 126 and/or wear a cap 124 while the employee 114 is participating in virtual games that are presented to the employee 114 via the VR headset 122, and the various health sensors 500 of the chair 126, the various health sensors 402 of the cap 124 and/or the various health sensors 306 of the VR headset 122 can be used to acquire the blood pressure (BP) respiratory rate (RR), hear rate (HR), blood glucose level, brain activity, and/or the like for the employee 114.

In some embodiments, the various chapters of the game can reflect various situations (e.g., tasks, challenges, or the like) typically faced by employees throughout the day. For example, a first chapter of a game (e.g., relating to "accountability and self-discipline") can include, presenting via the VR headset 122, a VR scene that includes preparing for and traveling to work. During this chapter, the employee 114 can make various decisions, such as sleeping-in (e.g., snoozing the alarm clock), dressing, showering, eating breakfast, watching television, reading the newspaper, and/or the like. In some embodiments, a score (e.g., 0-10) for the chapter can be determined based on what the employee 114 does and/or how she/he does them in the virtual environment. For example, participating in desirable actions, such as eating breakfast in the first chapter, may contribute to a higher score for the chapter, whereas participating in less desirable actions, such as sleeping-in in the first chapter, may contribute to a lower overall score for the first chapter. In some embodiments, the score may reflect the sensed health characteristics of the employee 114 while engaged in the chapter. For example, having desirable health characteristics, such as blood pressure (BP) respiratory rate (RR), hear rate (HR) and/or the like below a threshold level and/or brain activity above a threshold level, may contribute to a higher score for the chapter, whereas having less desirable health characteristics, such as blood pressure (BP) respiratory rate (RR), hear rate (HR) and/or the like above a threshold level and/or brain activity below a threshold level, may contribute to a higher score for the chapter.

A second chapter of the game (e.g., relating to "critical behaviors") can include, presenting via the VR headset 122, a VR scene that includes workplace scenarios that require planning, goal setting, tasks completion, troubleshooting, and/or the like by the employee 114. During this chapter, the employee 114 can, for example, organize/set her/his daily schedule, set one or more goals for the day, complete task in the VR environment (e.g., including task for the goals set), make troubleshooting decisions (e.g., reorganizing her/his schedule for the day when an event is presented that conflicts with the daily schedule), and/or the like. In some embodiments, a score (e.g., 0-10) for the chapter can be determined based on what the employee 114 does and/or how she/he does them in the virtual environment. For example, participating in desirable actions, such as scheduling her/his day when she/he arrives to her/his workstation in the morning, may contribute to a higher score for the chapter, whereas participating in less desirable actions, such as failing to complete a goal for the day, may contribute to a lower overall score for the second chapter. In some embodiments, the score may reflect the sensed health characteristics of the employee 114 while engaged in the chapter. For example, having desirable health characteristics, such as blood pressure (BP) respiratory rate (RR), hear rate (HR) and/or the like below a threshold level and/or brain activity above a threshold level, may contribute to a higher score for the chapter, whereas having less desirable health characteristics, such as blood pressure (BP) respiratory rate (RR), hear rate (HR) and/or the like above a threshold level and/or brain activity below a threshold level, may contribute to a higher score for the chapter.

A third chapter of the game (e.g., relating to "difficult interaction") can include, presenting via the VR headset 122, a VR scene that includes workplace scenarios that require the employee 114 to participate in difficult interactions (e.g., difficult conversations) with other persons, such as other employees, customers and/or the like in a virtual environment. These difficult interactions may be similar to interaction that a leader in the workplace may need to engage in during the course of her/his regular work duties. During this chapter, the employee 114 can, for example, conduct a virtual conversation with a virtual employee in which the employee 114 must communicate to the virtual employee that she/he needs to improve his/her work performance. In some embodiments, a score (e.g., 0-10) for the chapter can be determined based on what the employee 114 does and/or how she/he does them in the virtual environment. For example, participating in desirable actions, such as asking the other person if she/he has any questions, may contribute to a higher score for the chapter, whereas participating in less desirable actions, such as failing to give the other person a chance to respond, may contribute to a lower overall score for the third chapter. In some embodiments, the score may reflect the sensed health characteristics of the employee 114 while engaged in the chapter. For example, having desirable health characteristics, such as blood pressure (BP) respiratory rate (RR), hear rate (HR) and/or the like below a threshold level and/or brain activity above a threshold level, may contribute to a higher score for the chapter, whereas having less desirable health characteristics, such as blood pressure (BP) respiratory rate (RR), hear rate (HR) and/or the like above a threshold level and/or brain activity below a threshold level, may contribute to a higher score for the chapter.

A fourth chapter of the game (e.g., relating to "presentation skills") can include, presenting via the VR headset 122, a VR scene that includes a scenario in which the employee 114 is required to deliver one or more presentations to other virtual persons, such as other employees, customers and/or the like of a virtual environment. These presentations may be similar to presentations that a leader in the workplace may need to engage in during the course of her/his regular work duties. During this chapter, the employee 114 can, for example, deliver a presentation on quarterly performance of a particular group within the business, and/or the like. In some embodiments, a score (e.g., 0-10) for the chapter can be determined based on what the employee 114 does and/or how she/he does them in the virtual environment. For example, participating in desirable actions, such presenting without excessive movement, may contribute to a higher score for the chapter, whereas participating in less desirable actions, such as presenting in with excessive movement, may contribute to a lower overall score for the fourth chapter. In some embodiments, the score may reflect the sensed health characteristics of the employee 114 while engaged in the chapter. For example, having desirable health characteristics, such as blood pressure (BP) respiratory rate (RR), hear rate (HR) and/or the like below a threshold level and/or brain activity above a threshold level, may contribute to a higher score for the chapter, whereas having less desirable health characteristics, such as blood pressure (BP) respiratory rate (RR), hear rate (HR) and/or the like above a threshold level and/or brain activity below a threshold level, may contribute to a higher score for the chapter.

A fifth chapter of the game (e.g., relating to "employee health") can include, presenting via the VR headset 122, a VR scene that includes a scenario in which the employee 114 is required to complete various challenges that relate to employee wellbeing, energy management, self-care, mindfulness, resiliency and/or the like. These challenges may be similar to those described herein. During this chapter, the employee 114 can, for example, participate in, in a virtual environment, a reaction test (e.g., a drop test with scoring based how quickly the employee can catch a falling object), a coordination test (e.g., a catch test with scoring based how many objects the employee can catch in a given time period), a balance test (e.g., a one-leg test with scoring based on how long the employee is able to remain standing on the one leg), a foundational strength test (e.g., a plank test with scoring based on how long the employee is able to maintain a plank position), an endurance test (e.g., a squat test with scoring based on how long the employees is able to maintain a squatting position), a flexibility test (e.g., a sit and reach test with scoring based on how far the employee is able to reach), and/or the like. In some embodiments, a score (e.g., 0-10) for the chapter can be determined based on scores for the various challenges. For example, a score for the fourth chapter may be an sum, average or the like of the individual scores for the challenges undertaken in the fourth chapter. In some embodiments, the score may reflect the sensed health characteristics of the employee 114 while engaged in the chapter. For example, having desirable health characteristics, such as blood pressure (BP) respiratory rate (RR), hear rate (HR) and/or the like below a threshold level and/or brain activity above a threshold level, may contribute to a higher score for the chapter, whereas having less desirable health characteristics, such as blood pressure (BP) respiratory rate (RR), hear rate (HR) and/or the like above a threshold level and/or brain activity below a threshold level, may contribute to a higher score for the chapter.

As described herein, scores from one or more of the chapters can be used to determine a corresponding score for the employee 114. For example, a score for the employee 114 may be a sum of the scores for the first, second, third, fourth, and fifth chapters of the VR game. As described herein, in some embodiments, the scores from the one or more chapters can be used to generate a resiliency score for the employee that can be used to rank the employee 114 relative to other employees 114 (e.g., other candidates for leadership positions) and/or as a basis for automatic selection of the employee 114 for promotion into a leadership position. Thus, for example, employee participation in virtual chapters/situations for a work day can be used to assess the qualification of employees for leadership positions. For example, where each chapter has a possible score of 1-5, an employee 114 that has scores of 3, 4, 4, 5 and 3 for the five chapters may be determined to have a score of about 19 (total) or about 3.8 (an average of the scores). This score may be used as the resiliency score for the employee 114, or may at least be a contribution to an overall resiliency score for the employee 114.

In some embodiments, outputting corresponding resiliency data for the candidate employee (block 708) can include the resiliency data acquisition system 102 providing the acquired resiliency data 110 for an employee 114 to the employee leadership assessment system for processing. The resiliency data 110 can include some or all of the general health information, the health status data, and/or the functional performance data acquired for the employee 114. For example, the terminal 128 may consolidate some or all of the general health information, the health status data, and/or the functional performance data acquired for the employee 114 to generate corresponding resiliency data 110 for the employee 114, and may provide the resiliency data 110 to the employee leadership assessment (ELA) system 104.

As an example embodiment of the above described method 700 of acquiring employee resiliency data, John Smith, a candidate employee 114 for management at company XYZ, may make weekly visits to an LTC 120 located onsite at company XYZ's facilities. Upon arriving at the LTC 120, John may visit a terminal 128 at the LTC 120 and submit general health information via an interactive health evaluation form GUI presented at the terminal 128. The evaluation can include, for example, questions regarding his health risks, lifestyle, medical history, and/or the like. After completing the interactive health evaluation, John may take part in one or more health status tests to provide his health status data indicative of his current vital signs. This can include, for example, John sitting in a chair 126 and/or wearing a cap 124 while an automated suite of tests use the various sensors of the chair 126 and cap 124 to acquire John's blood pressure (BP) respiratory rate (RR), hear rate (HR), blood glucose level, brain activity, and/or the like. Further, after completing the one or more health status tests, John may take part in one or more functional performance tests to provide functional performance data indicative of one or more of his functional performance skills (e.g., his reaction skills, coordination skills, balance, flexibility, strength, endurance, and/or the like). This can include, for example, John completing different functional performance test, such as a reaction test (e.g., a drop test with scoring based how quickly the employee can catch a falling object), a coordination test (e.g., a catch test with scoring based how many objects the employee can catch in a given time period), a balance test (e.g., a one-leg test with scoring based on how long the employee is able to remain standing on the one leg), a foundational strength test (e.g., a plank test with scoring based on how long the employee is able to maintain a plank position), an endurance test (e.g., a squat test with scoring based on how long the employees is able to maintain a squatting position), a flexibility test (e.g., a sit and reach test with scoring based on how far the employee is able to reach), and/or the like. As described above, in some embodiments, one or more of the functional performance tests can be performed in a virtual environment (e.g., using virtual scenes provided by a VR headset 122 worn by John during testing). John's general health information, health status data and functional performance data may be consolidated and/or sent to the employee leadership assessment system 104 by the terminal 128.

Returning to method 600 or FIG. 6, in some embodiments, processing the employee resiliency data to generate employee leadership information (block 604) can include the employee leadership assessment (ELA) system 104 processing the resiliency data 110 to generate employee leadership information 112. In some embodiments, one or more algorithms can be applied to the resiliency data 110 for an employee 114 to generate one or more corresponding scores for the employee 114. For example, one or more lifestyle algorithms can be applied to the resiliency data 110 for an employee 114 to generate respective scores for various areas of the employee's life (e.g., physical environment, health and well-being, financial abundance, family and friends, career and job satisfaction, significant other, personal development and growth, and fun and recreation). As a further example, a resiliency algorithm can be applied to the resiliency data 110 for an employee 114 to generate a resiliency score for the employee 114. In some embodiments, the resiliency score for an employee 114 can be compared to resiliency scores for other employees 114 to provide for comparisons of employees' leadership potential and development. For example, employees 114 may be ranked based on resiliency scores, and employees 114 with the highest resiliency scores may be automatically recommended or selected for leadership positions or other promotions.

In some embodiments, a resiliency algorithm for the change over a period can be defined as follows:

$$\frac{dC}{dt} = 4.7 \times \mu \times \psi \times \left\{ \frac{LC^{(1-6)}}{dt} + \frac{X^{(1-2)}}{dt} + \frac{x^{(3-4)}}{dt} \right\} \quad (1)$$

where dC/dt is a total cost avoidance due to health and performance risk over time, $\psi$ is a total number (or population) of candidate employees for leadership positions, $\mu$ is medical costs avoided, $LC^{(1-6)}$ is a total sum of leadership competencies improvements, $X^{(1-2)}$ is a total sum of health status improvements, and $X^{(3-4)}$ is a total sum of functional performance improvements. The value of 4.7 may be arrived at based on a total cost avoided (or savings of) about $4.7. For example, where a ratio of indirect cost-to-direct cost of about 3.7 is determined, then each $1 of direct cost (e.g., medical cost) avoided may be associated with an indirect cost avoided of about $3.7, and a total cost avoided (or savings of) about $4.7. Consistent with the above equation, a 50% improvement of the course of a year attributable to the change in leadership competencies improvements, health status improvements and functional performance improvements, may realize a 50% reduction in total cost. For example, where for example, 4.7×μ×ψ is determined to be about $2.125 million, an improvement of about 50% in a year for the above factors may lead to a 1 year resiliency (or cost savings) of about $1.06 million (e.g., dC/dt=$2.125× 0.5/yr=$1.06 million/yr. Further, a number of risk avoided (ΔΓ) per year that can be attributed to the program may be determined based on a reduced chance of an employee having one risk per year (e.g., 4.85%) multiplied by the total number (or population) of candidate employees for leadership positions (ψ) (e.g., 1000) (e.g., ΔΓ=0.0485×1000=48.5 risk/year). Further, the total medical cost avoided per year that can be attributed to the program may be determined based on the number of risk avoided (ΔΓ) per year (e.g., 48.5 risk/year) multiplied by the cost per risk (e.g., $1500/risk) (e.g., ΔC=48.5 risk/year×$1500/risk=$72,750).

In some embodiments, a resiliency score for an employee 114 may be determined to be the total cost avoidance due to health and performance risk over time for the employee 114. In some embodiments, this resiliency may be a measure of the change in "cost avoidance" attributed to the employee 114 from a start time to a second/present time. For example, if a leadership development program begins on January 1st, each of the candidate employees 114 resiliency data 110 can be acquired for each of the employees 114 (e.g., at the LTC 120) on January 1st. Updated resiliency data 110 can be acquired periodically (e.g., weekly) for each of the employees 114 (e.g., via periodic visits to the LTC 120) on January 8th, January, 15th and so forth. A resiliency score for an employee 114 at a given time may be the total cost avoidance (dC/dt) over the latest period (e.g., on January 16th, the resiliency score for an employee 114 the total cost avoidance (dC/dt) for the employee 114 over the period from January 8th to January 15th), or the total cost avoidance (dC/dt) since the inception of the program (e.g., on January 16th, the resiliency score for an employee 114 is the total cost avoidance (dC/dt) for the employee 114 over the period from January 1st to January 15th).

In some embodiments, LC(1-6) is calculated through a cumulative scoring of the leadership competency scores (e.g., based on traditional and evidence based scoring systems). This can be given a total score of 100.

In some embodiments, X(3-4) is calculated through alignment of leadership skills and ability. Functions may include some or all of the following: the ability to react to unforeseen circumstances (reflex test with a score of 1-5); the ability to coordinate various functions at one time and maintain focus and direction (coordination test with a score of 1-5); the ability to balance, remain centered and committed to the cause despite external forces (balance test with a score of 1-5); the ability to have strong foundations (to the core) despite the turbulence to remain well positioned and in strong alignment (core test with a score of 1-5); the ability of endurance to keep going despite the discomfort and uncertainty in the sense of never giving up (endurance test with a score of 1-5); the ability to remain stable, yet flexible, extending the limits of stability within reason (flexibility test with a score of 1-5). Evaluation by normative data as related to age and gender (total score 1-30) can also be provided. Specific performance data may be selected based upon the physical manifestation of leadership abilities, skills and competencies. Data may, for example, be collated for functional performance (compared with normative data) based upon the alignment of leadership skills and ability. Each testing platform/area may provide a score, with X(3-4) being the total of those scores, divided by 30 (e.g., total score/30).

Figures 13, 14:
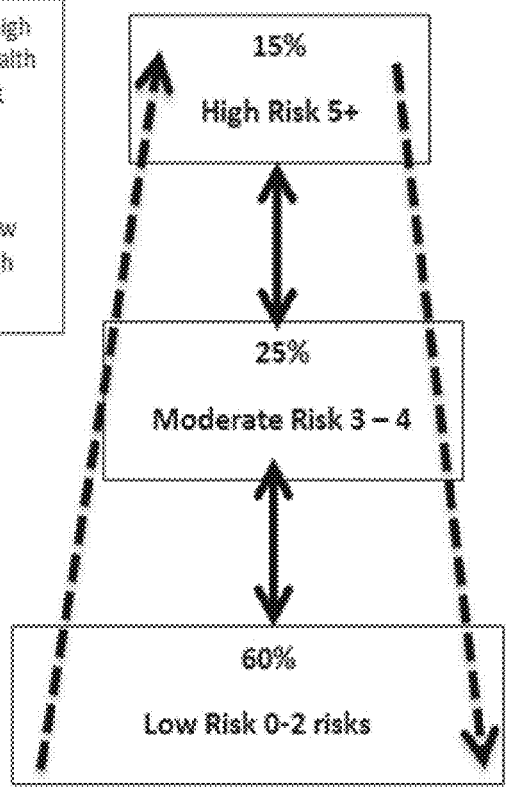
FIG. 13 is a table that illustrates examples of various biometric risk categories in accordance with one or more embodiments.
FIG. 14 is a diagram that illustrates an example risk profile and migration of risks and cost burden in accordance with one or more embodiments.

In some embodiments, X(1-2) is calculated through the actual scoring and collation of data for the combined physiological and psychosocial health risk scoring for each leader/employee determined by the number of indicators for each risk category (low, medium, high) incidence: chronic health conditions (number); lifestyle: fitness activity level (sedentary-athletic); biometrics 1: BMI; biometrics 2: fat percentage (%); biometrics 3: blood pressure (systolic and diastolic; mmHg); biometrics 4: heart rate (bpm). FIG. 13 is a table 1300 that illustrates examples of various biometric risk categories ins accordance with one or more embodiments. Table 1300 may represent standardized measures based on health risk and health status. Changes in costs can be calculated by applying the HERO study data sets. It can be determined that improved lifestyle behaviors and health conditions which can result in significant cost avoidance for a company (e.g., based on the healthcare cost accounting of the HERO study: medical premiums). For example, decreased cigarette smoking may equates to about $960 USD/employee/year; improved physical activity may equates to about $961 USD/employee/year; decreased stress may equates to about $1,718 USD/employee/year; decreased hypertension may equates to about $1,250 USD/employee/year; decreased pre-diabetes may equates to about $1,350 USD/employee/year. An evaluation (score) can be provided based on the following risk categories: low, medium or high. The scores can be based on the thresholds identified herein. FIG. 14 is a diagram that illustrates an example risk profile and migration of risks and cost burden 1400 in accordance with one or more embodiments. As illustrated, an example population profile may include the following risk distribution: Low=60%/Medium=25%/High=15%.

Figure 15:
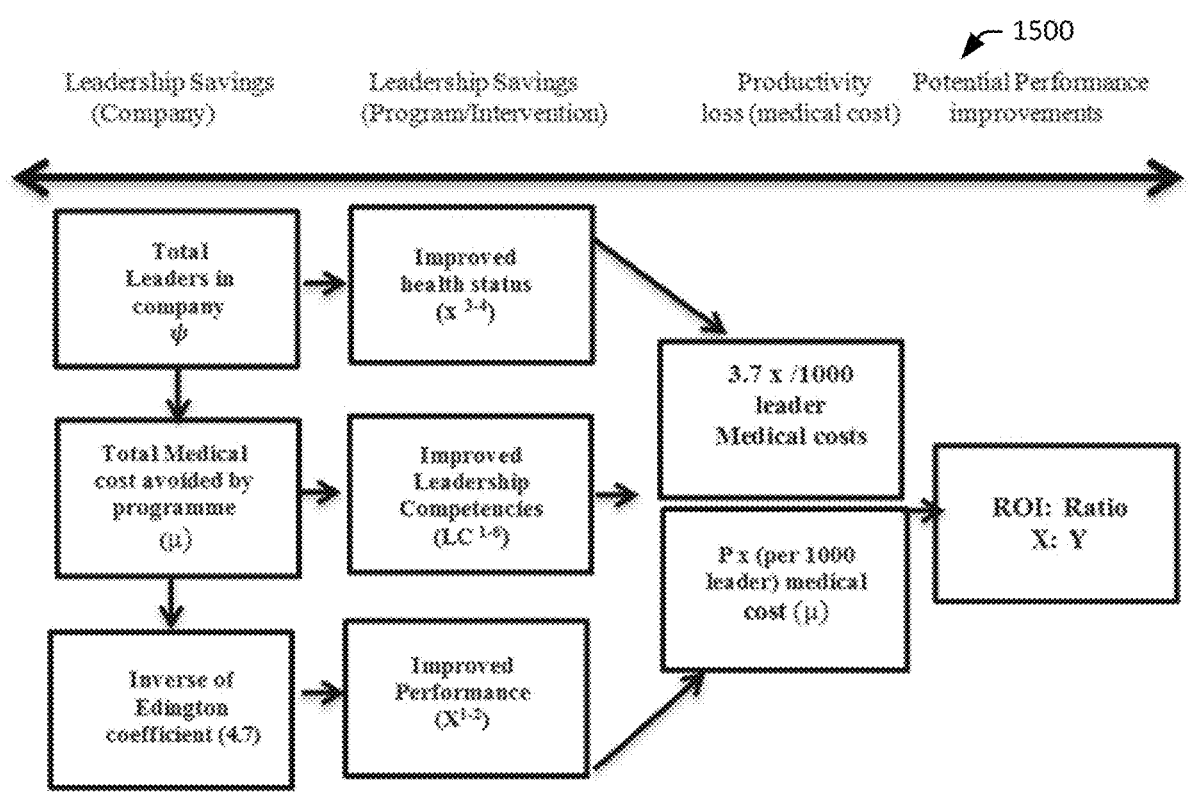
FIG. 15 is a diagram that illustrates relations between various factors of a resiliency algorithm, and a determination of return on investment (ROI) ratio in accordance with one or more embodiments.

In some embodiments, the resiliency data 110 can be used to generate scores for respective life areas. Specific lifestyle data may be selected as benchmarked on leadership work—life balance measurements. Employees 114 may be measured for their ability to balance on a 0-10 likert scale, with a scoring of 10 corresponding to about a 100% satisfaction in the quality and time dedicated to a corresponding dimension, and a scoring of 1 corresponding to about a 1% satisfaction in the corresponding dimension. Analysis of lifestyle factors and practices as related to eight key areas (each with a best score=10) can be used to generate an overall score (e.g., total of individual scores divided by 80). This may provide an initial platform on the reflection in the balance of life, and can indicate a gap analysis on work—life equilibrium and may identify areas of strengths and challenges. FIG. 15 is a diagram that illustrates relations between various factors of a resiliency algorithm, and a determination of return on investment (ROI) ratio in accordance with one or more embodiments.

FIGS. 16A and 16B are charts 1600 and 1602 that illustrate example physiological scores and performance test scores, respectively, for an employee in accordance with one or more embodiments. The scores may be based on the resiliency data 110 acquired. Based on these physiological scores and performance test scores, scores of about 9, 8, 9, 9, 8, 8, 7, and 9, for example, can be determined for the employee's life areas of physical environment, career and job satisfaction, financial abundance, health and well-being, family and friends, personal development, significant other, and fun and recreation, respectively. FIG. 17 is an example lifestyle spider diagram 1700 that graphically illustrates these scores for the employee's life areas. Such a diagram may be presented, for example, via a graphical user interface, such as the employee leadership dashboard 1000 or employer leadership dashboard 1100 discussed in more detail herein with regard to FIGS. 10 and 11A.

In some embodiments, providing employee leadership information for review (block 606) can include the employee leadership assessment system 104 providing employee leadership information 104 for one or more employees or groups of employees to one or more leadership review systems 106 for presentation to one or more employees 114 and/or one or more employers 116. For example, an employee 114 may log in to her/his account via a leadership review application of a leadership review system 106 (e.g., the employee's workstation), and submit a request to view his personal employee leadership dashboard. The employee leadership assessment system 104 may, in turn, serve employee leadership information 212, including her/his personal employee leadership dashboard, to the leadership review application for display to employee 114. As a further example, an employer 116 may log in to her/his account via a leadership review application of a leadership review system 106 (e.g., the employer's workstation), and submit a request to view an employer leadership review dashboard (e.g., an employer leadership review dashboard or an employer group leadership review dashboard). The employee leadership assessment system 104 may, in turn, serve employee leadership information 212, including her/his personal employee leadership dashboard, to the leadership review application for display to employee 114.

Figure 10:
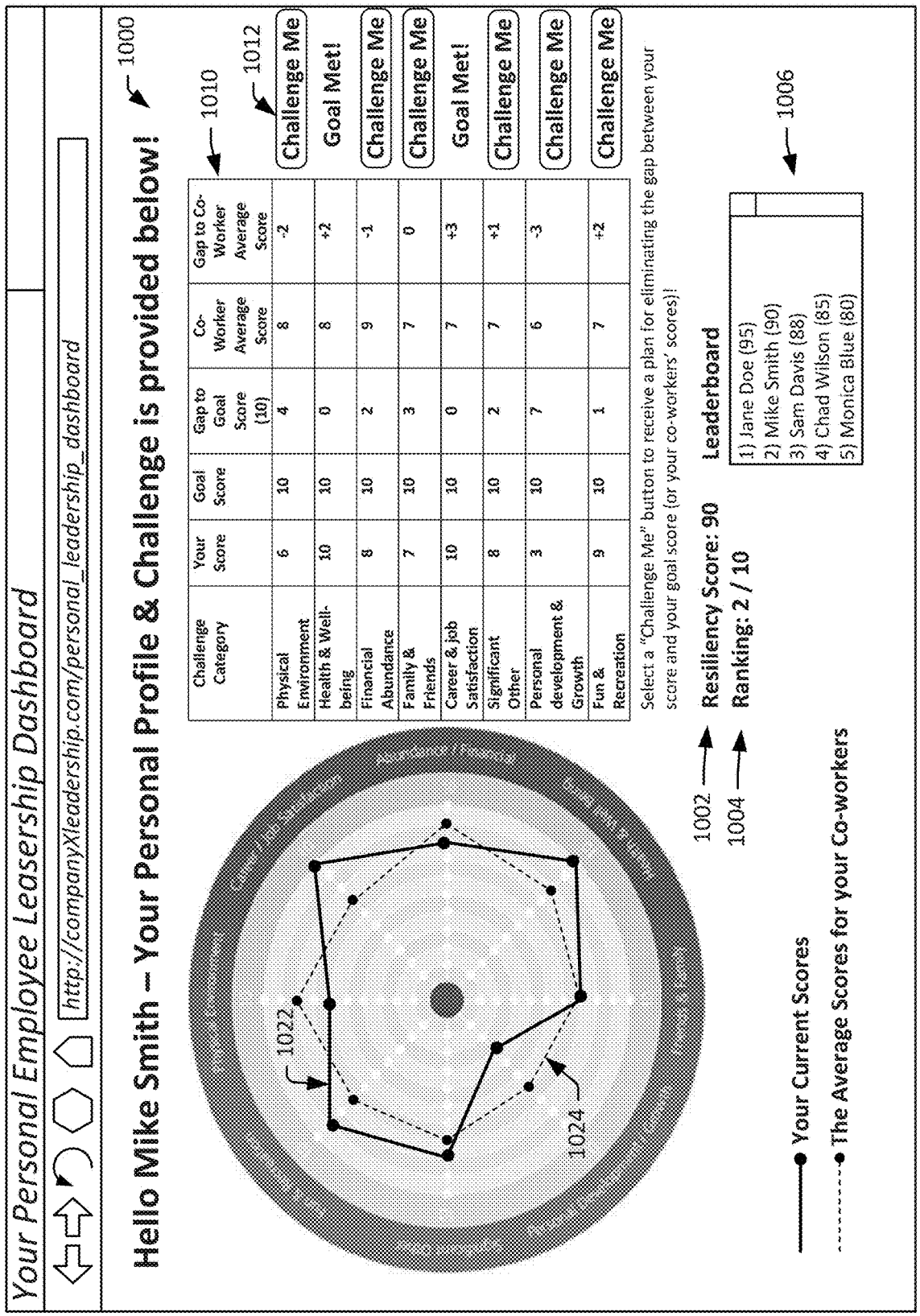
FIG. 10 is a diagram that illustrates an example employee leadership dashboard in accordance with one or more embodiments.

FIG. 10 is a diagram that illustrates an example employee leadership dashboard 1000 in accordance with one or more embodiments. Such a dashboard 1000 can be accessible by a particular employee 114 (e.g., John Smith) and can include leadership information for the employee 114. As depicted, an employee leadership dashboard 1000 can include, for example, a resiliency score 1002 for the employee 114, a ranking 1004 of the employee 114 relative to other employees 114 based on her/his resiliency score 1002, a leaderboard 1006 that includes a listing of the current employee rankings, a lifestyle spider diagram 1008 and/or lifestyle chart 1010 that indicates the scores for the employee 114 in various life areas, and/or interactive challenge links 1012 to challenges (or suggestions) for improving the various life areas and scores.

The resiliency score 1002 may include a current resiliency score for the employee 114 determined in accordance with the techniques described herein. For example, the resiliency score 1002 may reflect a change in resilience (C) over a given period of time (dC/dt), such as the last week, the last month, or since the start of the program. For example, if the leadership development program the employee 114 (e.g., John Smith) is participating in began on January 1st and the employee 114 is viewing the dashboard on February 10th, then the resiliency score 1002 may represent the change in the score for the employee 114 from January 1st to February 10th.

The ranking 1004 may include a current raking of the employee 114 relative to other employees 114 participating in the in the same leadership program as the employee 114. In some embodiments, the ranking 1004 can be based on the resiliency scores for each of the respective employees 114 participating in the same leadership program as the employee 114. For example, if the employee 114 (e.g., John Smith) has a resiliency score of 90, there are 10 employees 114 participating in the same leadership development program at the employee 114, and only one another employee 114 (e.g., Jane Doe) has a resiliency score higher than the employee 114, then the ranking for the employee 114 may be 2 out of 10. The leaderboard 1006 may include a listing of the current rankings of employees 114 participating in the leadership development program.

The lifestyle spider diagram 1008 and/or the lifestyle chart 1010 may indicate the scores for the employee 114 in various life areas. For example, the lifestyle spider diagram 1008 and the lifestyle chart 1010 may indicate scores of 1 to 10 for each of physical environment, health and well-being, financial abundance, family and friends, career and job satisfaction, significant other, personal development and growth, and fun and recreation. The spider diagram 1008 may provide an easy way for the employee 114 to quickly assess her/his strengths and weaknesses in the various life areas. In some embodiments, the spider diagram 1008 can include a first "web" 1022 indicative of the current scores for the employee 114 and a second "web" 1024 indicative of another set of scores, such as the average scores for co-workers (e.g., the average score for the other employees participating in the leadership program). The lifestyle chart 1010 may provide a detailed assessment of her/his strengths and weaknesses in the various life areas, including, for example, indications of goal scores, the average scores for co-workers, and differences (or "gaps") between the score for the employee 114 and those scores (e.g., the "gap to goal score" indicating a gap between the score for the employee 114 and the goal for the employee 114 and/or the "gap to co-worker average score" indicating a gap between the score for the employee 114 and the average score for the other employees 114 participating in the leadership program).

In some embodiments, the interactive challenge links 1012 can improve interactive links for navigating to challenges (or suggestions) for improving the various life areas and scores. For example, if the employee 114 has a relatively low score (e.g., below her/his goal score) for the "friends and family" life area, the dashboard 1000 may include a corresponding challenge link 1012 (e.g., a "Challenge me" button) that can be selected by the employee 114 to navigate to content that can help the employee 114 to improve that area of her/his life, and, thereby improve the score for that life area. In some embodiments, the content can include suggestions or instructions on how to improve the life area. For example, if the challenge link 1012 for the "friends and family" life area is selected, the employee 114 may be presented with a pop-up dialogue including the following suggestion: "For the next month, set aside 1 evening during each work week and ½ day during each weekend that is reserved for interacting with your family." In some embodiments, activities to improve a life area or an employee can be automatically implemented for the employee 114 (e.g., by the employee leadership assessment system 104). For example, the electronic work calendar for the employee 114 may be automatically populated with a calendar entry/event for "Family Time," 1 evening during each of the work weeks and a ½ day during each of the weekends of the following month. In some embodiments, similar calendar entries can be created for activities that may help to improve the respective life area. For example, if an employee 114 has a relatively low score for "physical environment", then upon selection of a corresponding challenge link 1012, the electronic work calendar for the employee 114 may be automatically populated with 1 hour calendar entry/event for "Take a walk outside" on each workday of the following month. As a further example, if an employee 114 has a relatively low score for "health & well-being", upon selection of a corresponding challenge link 1012, the electronic work calendar for the employee 114 may be automatically populated with 1 hour calendar entries/events for "Exercise" on 3 days a week for the following month. If an employee 114 has a relatively low score for "financial abundance", upon selection of a corresponding challenge link 1012, the electronic work calendar for the employee 114 may be automatically populated with 1 hour calendar entry/event for "Take a Financial Accounting" once a week for the following month. If an employee 114 has a relatively low score for "career & job satisfaction", upon selection of a corresponding challenge link 1012, the electronic work calendar for the employee 114 may be automatically populated with a 1 hour calendar entry/event for "Meet with Supervisor" at least once during the following month. If an employee 114 has a relatively low score for "significant other", upon selection of a corresponding challenge link 1012, the electronic work calendar for the employee 114 may be automatically populated with a 1 hour calendar entry/event for "Spouse Date Night" at least once a week for the following month. If an employee 114 has a relatively low score for "personal development & growth", upon selection of a corresponding challenge link 1012, the electronic work calendar for the employee 114 may be automatically populated with a 1 hour calendar entry/event for "Career and Personal Networking" at least once a week for the following month. If an employee 114 has a relatively low score for "fun and recreation", upon selection of a corresponding challenge link 1012, the electronic work calendar for the employee 114 may be automatically populated with calendar entries/events for "Team Sports" that correspond to workplace sports (e.g., work league soccer games) taking place during following month. Such automatic generation of calendar entries can encourage the employee 114 to make time for each of the activities, thereby helping the employee 114 to improve in each of the life areas.

FIG. 11A is a diagram that illustrates an example employer (employee) leadership review dashboard 1100 in accordance with one or more embodiments. An employer leadership review dashboard 1100 may provide information for a particular employee 114 or group of employees 114. For example, in the illustrated embodiment, the dashboard 1100 includes a "select employee/group to view" drop-down selection 1102 that enables the employer 116 viewing the dashboard 1100 to select which employee 114 or group of employees 114 she/he would like to view leadership information for. In the illustrated embodiment, the employee 114 "Mike Smith" is selected, and the dashboard 1100 is populated with information about the employee 114 Mike Smith. In other embodiments, the employer 116 may select the employee 114 "Jane Doe" via the drop-down selection 1102, and the dashboard 1100 may be populated with information about Jane Doe. Or, the employer 116 may select the group of employees 114 "Management Candidates—Sales" via the drop-down selection 1102, and the dashboard 1100 may be populated with information about the corresponding group of employees 114.

In some embodiment, the leadership review dashboard 1100 can provide for comparison of a particular employee 114 to another employee 114 or group of employees 114. For example, in the illustrated embodiment, the dashboard 1100 includes a "select employee/group to compare" drop-down selection 1104 that enables the employer 116 viewing the dashboard 1100 to select which employee 114 or group of employees 114 she/he would like to compare the selected employee 114 or group of employees (e.g., selected via drop-down selection 1102) she/he would like to use as comparison. In the illustrated embodiment, the group of employees 114 in "Management Candidates—Engineering" is selected, and the dashboard 1100 is populated with information that can be used to compare the selected employee 114 (Mike Smith) to the employees 114 in the "Management candidates—Engineering" group.

In some embodiments, the leadership information can include, for the selected employee 114 or group of employees 114, a resiliency score, a ranking of the employee/group relative to other employees/groups based on resiliency scores, a leaderboard that includes a listing of the current employee rankings, a lifestyle spider diagram and/or chart that indicates the employee's/group's scores in various life areas, an indication of whether an employee is recommended for promotion to management, a listing of employees that are recommended for promotion to management, and/or the like.

As depicted, employer leadership review dashboard 1100 can include, for example, a resiliency score 1112, a ranking 1114, a leaderboard 1116, a lifestyle spider diagram 1118 and/or lifestyle chart 1120, a promotion recommendation 1126, and/or a listing of employees recommended for promotion 1128.

The resiliency score 1002 may include a current resiliency score for a selected employee 114 (e.g., an employee 114 selected via drop-down selection 1104) or an average resiliency score for the employees 114 in a selected group (e.g., a group of employees 114 selected via drop-down selection 1104).

The ranking 1004 may include a current raking of a selected employee 114 (e.g., an employee 114 selected via drop-down selection 1104) relative to other employees 114 participating in the same leadership program as the selected employee 114. In some embodiments, if a group of employees 114 is selected (e.g., selected via drop-down selection 1102), a ranking 114 may not be displayed. In some embodiments, the ranking 1004 can be based on the resiliency scores for each of the respective employees 114 participating in the same leadership program as the selected employee 114. For example, if the employee 114 (e.g., John Smith) has a resiliency score of 90, there are 10 employees 114 participating in the leadership development program and only one other employee 114 (e.g., Jane Doe) has a resiliency score higher than the employee 114, then the ranking for the employee 114 may be 2 out of 10. In some embodiments, if an individual employee 114 is selected (e.g., selected via drop-down selection 1102), then the leaderboard 1116 may include a listing of the current rankings of employees 114 participating in the same leadership program as the selected employee 114. In some embodiments, if a group of employees 114 is selected (e.g., selected via drop-down selection 1102), then the leaderboard 1116 may include a listing of the current rankings of employees 114 in the selected group.

The lifestyle spider diagram 1118 and/or the lifestyle chart 1120 may indicate the scores for the selected employee 114 or group of employees 114 in various life areas. For example, the lifestyle spider diagram 1008 and the lifestyle chart 1010 may indicate scores of 1 to 10 for each of physical environment, health and well-being, financial abundance, family and friends, career and job satisfaction, significant other, personal development and growth, and fun and recreation. In some embodiments, if an individual employee 114 is selected (e.g., selected via drop-down selection 1102), then the scores for the life areas may be the corresponding scores for the employee 114. In some embodiments, if a group of employees 114 is selected (e.g., selected via drop-down selection 1102), then the scores for the life areas may be the averages of the respective scores for the employees 114 in the selected group. In some embodiments, the spider diagram 1008 can include a first "web" 1122 indicative of the current scores for the selected employee 114 or group of employees 114 (e.g., selected via drop-down selection 1102), and a second "web" 1124 indicative of another set of scores, such as those for the employee 114 or the group of employees 114 selected for comparison (e.g., selected via drop-down selection 1104). In some embodiments, if an individual employee 114 is selected for comparison (e.g., selected via drop-down selection 1104), then the scores for the life areas of the second web 1124 may be the corresponding scores for the employee 114. In some embodiments, if a group of employees 114 is selected for comparison (e.g., selected via drop-down selection 1104), then the scores for the life areas of the second web 1124 may be the averages of the respective scores for the employees 114 in the selected group.

The lifestyle chart 1120 may provide a detailed assessment of the strengths and weaknesses of the selected employee 114 or group of employees 114 (e.g., selected via drop-down selection 1102) in the various life areas, including, for example, indications of goal scores, the score for the employee 114 or group of employees 114 selected for comparison (e.g., selected via drop-down selection 1104), and differences (or "gaps") between the score for the selected employee 114 or group of employees 114 (e.g., selected via drop-down selection 1102) and those scores (e.g., the "gap to goal score" indicating a gap between the score for the selected employee 114 or group of employees 114 (e.g., selected via drop-down selection 1102) and the goal score and/or the "gap to comparison employee/group average score" indicating a gap between the score for the selected employee 114 or group of employees 114 (e.g., selected via drop-down selection 1102) and the average score for the employee 114 or the group of employees 114 selected for comparison (e.g., selected via drop-down selection 1104).

In some embodiments, if an individual employee 114 is selected (e.g., selected via drop-down selection 1102), then the promotion recommendation 1126 may indicate whether the employee 114 is recommended for a promotion. In some embodiments, an employee 114 is determined to be recommended for a promotion if it is determined that she/he has a resiliency score that satisfies a resiliency score threshold (e.g., she/he has a resiliency score that is at or above a predetermined resiliency score of 90). In some embodiments, an employee 114 is determined to not be recommended for a promotion if it is determined that she/he does not have a resiliency score that satisfies a resiliency score threshold (e.g., she/he has a resiliency score that is below a predetermined resiliency score of 90).

In some embodiments, the listing of employees recommended for promotion 1128 provides a listing of candidate employees 114 that are recommended for a promotion. In some embodiments, if an individual employee 114 is selected (e.g., selected via drop-down selection 1102), then the listing of candidate employees 114 may include a listing of the candidate employees 114 participating in the same leadership program as the selected employee 114 that have a resiliency score that satisfies a resiliency score threshold. In some embodiments, if a group of employees 114 is selected (e.g., selected via drop-down selection 1102), then the listing of candidate employees 114 may include a listing of the candidate employees 114 in the group that have a resiliency score that satisfies a resiliency score threshold.

FIG. 11B is a diagram that illustrates an example employer (group) leadership review dashboard 1150 in accordance with one or more embodiments. An employer group leadership review dashboard 1150 may provide information for a selected group of employees 114. For example, in the illustrated embodiment, the dashboard 1150 includes a "select group to view" drop-down selection 1152 that enables the employer 116 viewing the dashboard 1150 to select which employee or group of employees 114 she/he would like to view information for. In the illustrated embodiment, the employee group 114 "Management Candidates—Engineering" is selected, and the dashboard 1150 is populated with information about the corresponding group of employees 114. In other embodiments, the employer 116 may be able to select a group of employees 114 "Management Candidates—Sales" via the drop-down selection 1102, and the dashboard 1100 may be populated with information about the corresponding group of employees 114.

As depicted, an employer group leadership review dashboard 1150 may include, for example, a leaderboard 1154, a listing of employees recommended for promotion 1156, and various informational charts 1158 for the group of employees 114.

In some embodiments, the leaderboard 1154 may include a listing of the current rankings of employees 114 in the selected group of employees 114 (e.g., selected via drop-down selection 1152). For example, the leaderboard 1154 may include a listing of the current rankings of employees 114 in the selected group based on the respective resiliency scores for the employees 114. In some embodiments, the listing of employees recommended for promotion 1156 provides a listing of candidate employees 114 of the selected group of employees 114 (e.g., selected via drop-down selection 1152) that are recommended for a promotion. For example, the listing of candidate employees 114 may include a listing of the candidate employees 114 in the selected group of employees 114 that have a resiliency score that satisfies a resiliency score threshold. The charts 1158 may include a health risks chart 1160 (e.g., illustrating the distribution of health risks for the selected group of employees 114), body mass index chart 1162 (e.g., illustrating the distribution of body mass index for the selected group of employees 114), a functional performance level chart 1164 (e.g., illustrating the distribution of functional performance levels for the selected group of employees 114), a lifestyles chart 1166 (e.g., illustrating a percentage of the employees 114 in the selected group of employees 114 that engage in various types of lifestyles), a lifestyle mapping insights chart 1168 (e.g., illustrating the distribution of scores/categories for the employees 114 in the selected group of employees 114 in each life area of a set of life areas), and a functional performance insights chart 1170 (e.g., illustrating the distribution of scores/categories for the employees 114 in the selected group of employees 114 in each functional area of a set of functional areas).

Figure 12:
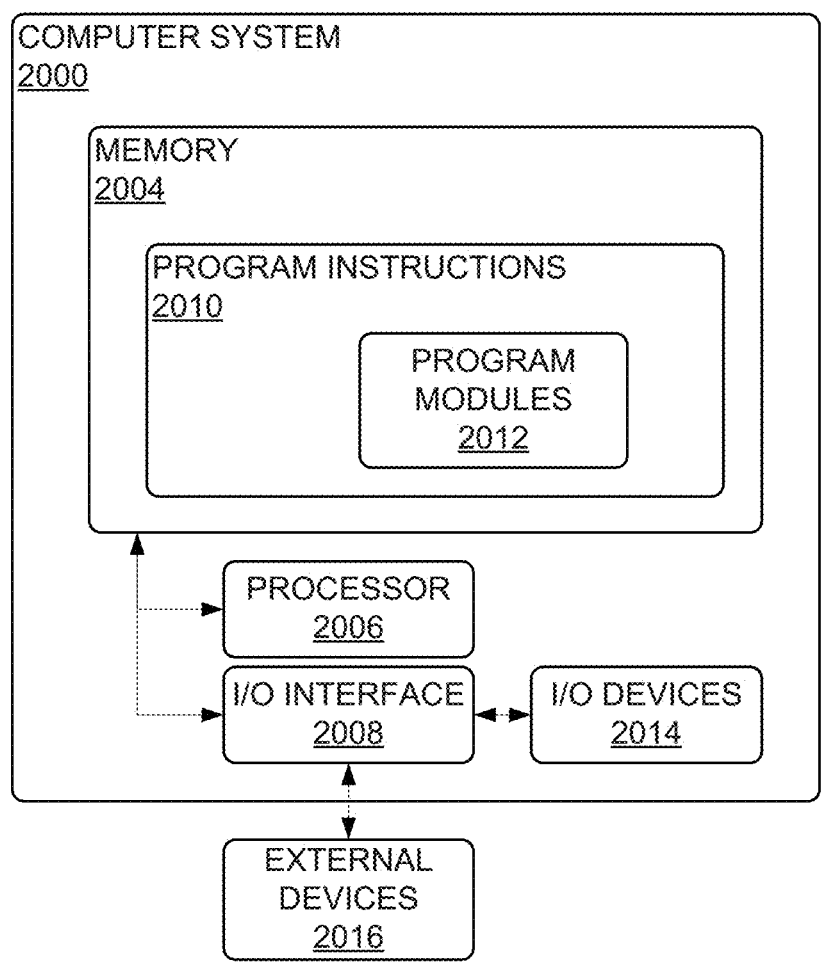
FIG. 12 is a diagram that illustrates an example computer system in accordance with one or more embodiments.

FIG. 12 is a diagram that illustrates an example computer system 2000 in accordance with one or more embodiments. In some embodiments, the computer system 2000 may include a memory 2004, a processor 2006, and an input/output (I/O) interface 2008. The memory 2004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 2004 may include a non-transitory computer-readable storage medium having program instructions 2010 stored therein. The program instructions 2010 may include program modules 2012 that are executable by a computer processor (e.g., the processor 2006) to cause the functional operations described herein, including those described with regard to the processes described herein, including some or all of the operations of methods 600 and 700. In the context of a computer system of a terminal 128, the program modules 2012 may include one or more modules for performing some or all of the operations described with regard to the terminal 128. In the context of a computer system of the employee leadership assessment system 104 (e.g., a server of the system 104), the program modules 2012 may include one or more modules for performing some or all of the operations described with regard to the employee leadership assessment system 104. In the context of a computer system of the leadership review system 106 (e.g., a computer of the system 106), the program modules 2012 may include one or more modules for performing some or all of the operations described with regard to the leadership review system 106.

The processor 2006 may be any suitable processor capable of executing/performing program instructions. The processor 2006 may include a central processing unit (CPU) that carries out program instructions (e.g., the program instructions of the program module(s) 2012) to perform the arithmetical, logical, and input/output operations described herein. The processor 2006 may include one or more processors. The I/O interface 2008 may provide an interface for communication with one or more I/O devices 2014, such as a joystick, a computer mouse, a keyboard, a display screen (e.g., an electronic display for displaying a graphical user interface (GUI)), and/or the like. The I/O devices 2014 may include one or more of the user input devices. The I/O devices 2014 may be connected to the I/O interface 2008 via a wired or a wireless connection. The I/O interface 2008 may provide an interface for communication with one or more external devices 2016, such as other computers (e.g., communicatively coupled to the network 108), one or more networks (e.g., the network 108), and/or the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. An employee management system comprising:
   an employee resiliency data acquisition system comprising:
   a terminal configured to acquire health information for an employee via an interactive health survey;
   one or more health sensor systems configured to acquire health status data for the employee; and
   an augmented virtual reality (AVR) headset configured to be worn about the head of the employee, the AVR headset being configured to present, for viewing by the employee, a functional performance test comprising a virtual scene comprising one or more virtual objects for the employee to interact with, and the AVR headset being configured to generate functional performance test data for the employee that is indicative of the interactions of the employee with the one or more virtual objects, wherein the AVR headset comprises one or more electroencephalogram (EEG) sensors configured to contact at least a portion of a scalp of the employee while the employee is wearing the AVR headset, and
   wherein the one or more health sensor systems comprise the one or more EEG sensors, and wherein the health status data for the employee comprises brain activity data for the employee acquired via the EEG sensors; and
   an employee leadership assessment system communicatively coupled to the employee resiliency data acquisition system via a communications network, the employee leadership assessment system comprising a non-transitory computer readable storage medium comprising program instructions stored thereon that are executable by one or more processors to cause:
   receiving, from the employee resiliency data acquisition system, a set of resiliency data for the employee, the set of resiliency data corresponding to the health information for the employee, the health status data for the employee, and the functional performance test data for the employee;

determining a resiliency score for the employee based at least in part on the set of resiliency data, the resiliency score indicating a change in a cost associated with the employee over a given period of time;

determining that the employee is recommended for a promotion to a leadership position within an organization based at least in part on the resiliency score;

determining a ranking of the employee relative to other employees within the organization based at least in part on the resiliency score;

serving, to a first device for display to the employee, an employee leadership review dashboard comprising:
an indication of the resiliency score for the employee; and
an indication of the ranking of the employee relative to the other employees;

serving, to a second device for display to an employer, an employer leadership review dashboard comprising:
an indication of the resiliency score for the employee;
an indication that the employee is recommended for the promotion to the leadership position within the organization; and
an indication of the ranking of the employee relative to the other employees;

determining an activity to be completed by the employee based at least in part on the resiliency score; and scheduling, on a work schedule for the employee, the activity for completion by the employee.

2. The system of claim 1, wherein the functional performance test comprises a reaction-drop test and the virtual scene comprises a virtual object appearing to fall in a field of view (FOV) of the employee, and wherein the employee is tasked with catching the virtual object.

3. The system of claim 1, wherein the functional performance test comprises a coordination-catch test and the virtual scene comprises multiple virtual objects appearing to move toward the employee in the field of view (FOV) of the employee, and wherein the employee is tasked with catching the one or more virtual objects.

4. The system of claim 1, wherein the one or more health sensor systems comprise a chair comprising one or more health sensors integrated into at least one of a seat bottom, a seat back, an arm rest and a headrest of the chair, wherein the one or more health sensors are configured to contact the employee when the employee is seated in the chair.

5. The system of claim 1, wherein the one or more health sensor systems comprise a cap configured to be worn by the employee, and wherein the cap comprises one or more EEG sensors located in an interior of the cap such that the EEG sensors contact at least a portion of the scalp of the employee while the employee is wearing the cap.

6. The system of claim 1, wherein the one or more EEG sensors are located in an interior of the AVR headset such that the EEG sensors contact at least a portion of the scalp of the employee while the employee is wearing the AVR headset.

7. The system of claim 1, wherein the set of resiliency data is associated with a first time, and wherein the program instructions stored thereon that are executable by one or more processors to cause:
receiving, from the employee resiliency data acquisition system, a second set of resiliency data for the employee, the second resiliency data corresponding to health information for the employee at a second time, health status data for the employee at the second time, and functional performance test data for the employee at the second time,
wherein the resiliency score is determined as a difference between a first value determined based on the set of resiliency data associated with the first time, and a second value determined based on the second set of resiliency data associated with the second time.

8. The system of claim 1, wherein the employee is a participant in an employee leadership program, and wherein the employer leadership review dashboard comprises a spider diagram comprising a first web indicative of a set of scores for the employee in one or more life areas, and a second web indicative of a set of scores for a group of employees participating in employee leadership program in the one or more life areas.

9. The system of claim 1, wherein the employee leadership review dashboard comprises a challenge link corresponding to a life area, and wherein the employee leadership review dashboard is configured to, in response to selection of the challenge link, display content suggestions for the employee to improve in the life area.

10. The system of claim 1, wherein the employee leadership review dashboard comprises a challenge link corresponding to a life area, wherein the activity to be completed by the employee based at least in part on the resiliency score is expected to improve the life area for the employee, and wherein the program instructions are further executable by the one or more processors to cause:
receiving a selection of the challenge link;
in response to receiving the selection of the challenge link, scheduling the activity for completion by the employee.

11. The system of claim 10, wherein scheduling the activity for completion by the employee comprises automatically adding one or more calendar events for the activity to an electronic calendar for the employee.

12. The system of claim 1, wherein the program instructions are further executable by the one or more processors to cause:
determining a score for the employee in a life area based at least in part on the set of resiliency data;
determining whether the score for the employee in the life area satisfies a life area score threshold; and
in response to determine that the score for the employee in the life area does not satisfy the life area score threshold, automatically scheduling one or more activities for the employee that are expected to improve the life area for the employee.

13. A method comprising:
acquiring, by an employee management system, a set of resiliency data for an employee, the resiliency data comprising:
health information for the employee acquired via an interactive health survey;
health status data for the employee acquired via one or more health sensor systems; and
functional performance test data for the employee, the functional performance test data acquired via a virtual performance test conducted using an augmented virtual reality (AVR) headset worn about the head of the employee and presenting, for viewing by the employee, a functional performance test comprising a virtual scene comprising one or more virtual objects for the employee to interact with, and the functional performance test data for the employee being indicative of the interactions of the employee with the one or more virtual objects, wherein the AVR headset comprises one or more electroencephalogram (EEG) sensors configured to contact at least a portion of a scalp of the employee while the employee is wearing the AVR headset, and wherein the one or more health sensor systems comprise the one or more EEG sensors, and wherein the health status data for the employee comprises brain activity data for the employee acquired via the EEG sensors;

determining, by the employee management system, a resiliency score for the employee based at least in part on the set of resiliency data, the resiliency score indicating a change in a cost associated with the employee over a given period of time;

determining, by the employee management system, that the employee is recommended for a promotion to a leadership position within an organization based at least in part on the resiliency score;

determining, by the employee management system, a ranking of the employee relative to other employees within the organization based at least in part on the resiliency score;

serving, by the employee management system to a first device for display to the employee, an employee leadership review dashboard comprising:
  an indication of the resiliency score for the employee; and
  an indication of the ranking of the employee relative to the other employees;

determining, by the employee management system, an activity to be completed by the employee based at least in part on the resiliency score;

scheduling, by the employee management system on a work schedule for the employee, the activity for completion by the employee; and completing, by the employee, the activity.

14. The method of claim 13, further comprising:
serving, by the employee management system to a second device for display to an employer, an employer leadership review dashboard comprising:
  an indication of the resiliency score for the employee;
  an indication that the employee is recommended for the promotion to the leadership position within the organization; and
  an indication of the ranking of the employee relative to the other employees.

15. The method of claim 13, wherein the set of resiliency data is associated with a first time, the method further comprising:
receiving, by the employee management system, a second set of resiliency data for the employee, the second resiliency data corresponding to health information for the employee at a second time, health status data for the employee at the second time, and functional performance test data for the employee at the second time,
wherein the resiliency score is determined as a difference between a first value determined based on the set of resiliency data associated with the first time, and a second value determined based on the second set of resiliency data associated with the second time.

16. The method of claim 13, further comprising:
determining, by the employee management system, a score for the employee in a life area based at least in part on the set of resiliency data;

determining, by the employee management system, whether the score for the employee in the life area satisfies a life area score threshold; and in response to determine that the score for the employee in the life area does not satisfy the life area score threshold, automatically scheduling, by the employee management system, one or more activities for the employee that are expected to improve the life area for the employee.

17. A non-transitory computer readable storage medium comprising program instructions stored thereon that are executable by one or more processors to cause:
acquiring, by an employee management system, a set of resiliency data for an employee, the resiliency data comprising:
  health information for the employee acquired via an interactive health survey;
  health status data for the employee acquired via one or more health sensor systems; and
  functional performance test data for the employee, the functional performance test data acquired via a virtual performance test conducted using an augmented virtual reality (AVR) headset worn about the head of the employee and presenting, for viewing by the employee, a functional performance test comprising a virtual scene comprising one or more virtual objects for the employee to interact with, and the functional performance test data for the employee being indicative of the interactions of the employee with the one or more virtual objects, wherein the AVR headset comprises one or more electroencephalogram (EEG) sensors configured to contact at least a portion of a scalp of the employee while the employee is wearing the AVR headset, and wherein the one or more health sensor systems comprise the one or more electroencephalogram (EEG) sensors, and wherein the health status data for the employee comprises brain activity data for the employee acquired via the EEG sensors;

determining, by the employee management system, a resiliency score for the employee based at least in part on the set of resiliency data, the resiliency score indicating a change in a cost associated with the employee over a given period of time;

determining, by the employee management system, that the employee is recommended for promotion to a leadership position within an organization based at least in part on the resiliency score;

determining, by the employee management system, a ranking of the employee relative to other employees within the organization based at least in part on the resiliency score;

serving, by the employee management system to a first device for display to the employee, an employee leadership review dashboard comprising:
  an indication of the resiliency score for the employee; and
  an indication of the ranking of the employee relative to the other employees;

determining, by the employee management system, an activity to be completed by the employee based at least in part on the resiliency score; and scheduling, by the employee management system on a work schedule for the employee, the activity for completion by the employee.

18. The medium of claim 17, wherein the program instructions are further executable by the one or more processors to cause:
  serving, by the employee management system to a second device for display to an employer, an employer leadership review dashboard comprising:
    an indication of the resiliency score for the employee;
    an indication that the employee is recommended for the promotion to the leadership position within the organization; and
    an indication of the ranking of the employee relative to the other employees.

19. The medium of claim 17, wherein the set of resiliency data is associated with a first time, and wherein the program instructions are further executable by the one or more processors to cause:
  receiving, by the employee management system, a second set of resiliency data for the employee, the second resiliency data corresponding to health information for the employee at a second time, health status data for the employee at the second time, and functional performance test data for the employee at the second time,
  wherein the resiliency score is determined as a difference between a first value determined based on the set of resiliency data associated with the first time, and a second value determined based on the second set of resiliency data associated with the second time.

20. The medium of claim 17, wherein the program instructions are further executable by the one or more processors to cause:
  determining, by the employee management system, a score for the employee in a life area based at least in part on the set of resiliency data;
  determining, by the employee management system, whether the score for the employee in the life area satisfies a life area score threshold; and
  in response to determine that the score for the employee in the life area does not satisfy the life area score threshold, automatically scheduling, by the employee management system, one or more activities for the employee that are expected to improve the life area for the employee.

21. An employee management system comprising:
  an employee resiliency data acquisition system comprising:
    a virtual reality (VR) headset configured to be worn about the head of the employee and to present one or more virtual testing scenarios to the employee, the VR headset comprising a tracking device for tracking arm and hand movements of the employee while wearing the VR headset, the VR headset comprising one or more electroencephalogram (EEG) sensors configured to contact at least a portion of a scalp of the employee while the employee is wearing the VR headset; and
    a health sensor system configured to acquire health status data indicative of health conditions of the employee, wherein the health sensor system comprises the one or more EEG sensors, and wherein the health status data for the employee comprises brain activity data for the employee acquired via the EEG sensors; and
  an employee leadership assessment system communicatively coupled to the employee resiliency data acquisition system via a communications network, the employee leadership assessment system comprising a non-transitory computer readable storage medium comprising program instructions stored thereon that are executable by one or more processors to cause:
    displaying, via the VR headset, a plurality of testing scenarios to the employee, wherein at least one of the testing scenarios comprises a situation faced by the employee during a workday, and wherein at least one of the testing scenarios comprises a functional performance test;
    obtaining, from the health sensor system, a set of resiliency data for the employee, the set of resiliency data comprising health status data indicative of performance of the employee in the plurality of testing scenarios displayed via the VR headset, and health conditions of the employee while engaged in the plurality of testing scenarios displayed via the VR headset;
    determining a resiliency score for the employee based at least in part on the set of resiliency data;
    determining that the employee is recommended for a promotion to a leadership position within an organization based at least in part on the resiliency score;
    determining a ranking of the employee relative to other employees within the organization based at least in part on the resiliency score;
    serving, to a first device for display to the employee, an employee leadership review dashboard comprising:
      an indication of the resiliency score for the employee; and
      an indication of the ranking of the employee relative to the other employees;
    serving, to a second device for display to an employer, an employer leadership review dashboard comprising:
      an indication of the resiliency score for the employee;
      an indication that the employee is recommended for the promotion to the leadership position within the organization; and
      an indication of the ranking of the employee relative to the other employees;
    determining an activity to be completed by the employee based at least in part on the resiliency score; and
    scheduling, on a work schedule for the employee, the activity for completion by the employee.

* * * * *